United States Patent [19]
Alig et al.

[11] Patent Number: 5,399,585
[45] Date of Patent: Mar. 21, 1995

[54] CARBOXAMIDES AND SULFONAMIDES COMPOUNDS WHICH HAVE USEFUL PHARMACEUTICAL UTILITY

[75] Inventors: Leo Alig, Kaiseraugst; Albrecht Edenhofer, Riehen; Marcel Müller, Frenkendorf, all of Switzerland; Arnold Trzeciak, Schopfheim, Germany; Thomas Weller, Basel, Switzerland

[73] Assignee: Hoffmann-La Roche Inc., Nutley, N.J.

[21] Appl. No.: 114,415

[22] Filed: Aug. 30, 1993

Related U.S. Application Data

[62] Division of Ser. No. 755,960, Sep. 6, 1991, Pat. No. 5,256,812, which is a division of Ser. No. 465,858, Jan. 16, 1990, Pat. No. 5,084,466.

[30] Foreign Application Priority Data

Jan. 31, 1989 [CH] Switzerland ............................ 326/89
Nov. 13, 1989 [CH] Switzerland .......................... 4069/89

[51] Int. Cl.$^6$ ................... C07D 333/10; A61K 31/38
[52] U.S. Cl. ..................... 514/438; 514/445; 514/447; 549/63; 549/65; 549/66; 549/68; 549/69; 549/77; 549/79
[58] Field of Search ............ 549/63, 66, 68, 69, 549/77, 65, 79; 514/445, 447, 438

[56] References Cited

U.S. PATENT DOCUMENTS

| | | | |
|---|---|---|---|
| 4,537,896 | 8/1985 | Claeson et al. | 514/330 |
| 4,746,737 | 5/1988 | Fujii et al. | 540/575 |
| 4,866,196 | 9/1989 | Iwakuma et al. | 562/430 |

FOREIGN PATENT DOCUMENTS

| | | | |
|---|---|---|---|
| 239907 | 10/1987 | European Pat. Off. | 546/304 |
| 325245 | 1/1989 | European Pat. Off. | 549/80 |
| M3656 | 2/1964 | France | 562/575 |
| 2007663 | 11/1978 | United Kingdom | 540/575 |

OTHER PUBLICATIONS

Derwent Abstract of 51899B, filed Sep. 11, 1977.
Saiki, Ikuo et al., Japn. J. Cancer Res., 81:660 (1990).
Cook, Nigel S. et al., TIPS Reviews, pp. 444–445, (1990).
Saiki, Ikuo et al., Br. J. Cancer, 60(5), pp. 722–728 (1989).
Knudsen, Karen A. et al., Exp. Cell Res., 179, pp. 42–49 (1988).

*Primary Examiner*—C. Warren Ivy
*Assistant Examiner*—Zinna N. Davis
*Attorney, Agent, or Firm*—George M. Gould; George W. Johnston; Alan P. Kass

[57] ABSTRACT

Novel carboxamides and sulfonamides are described having of the formula

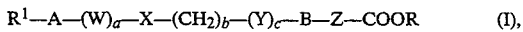

$$R^1\text{---}A\text{---}(W)_a\text{---}X\text{---}(CH_2)_b\text{---}(Y)_c\text{---}B\text{---}Z\text{---}COOR \qquad (I),$$

in which $R^1$, A, W, X, Y, B, Z, R, a, b and c are as provided in the description. These compounds are useful in the treatment of thromboses, apoplexy, myocardial infarct, inflammations, arteriosclerosis as well as in the treatment and prevention of tumors. These novel compounds are prepared by eliminating the protective groups in corresponding compounds with protected amidino or guanidino groups.

19 Claims, No Drawings

CARBOXAMIDES AND SULFONAMIDES COMPOUNDS WHICH HAVE USEFUL PHARMACEUTICAL UTILITY

This is a division of application Ser. No. 07/755,960, filed Sep. 6, 1991, now U.S. Pat. No. 5,256,812, which is a division of application Ser. No. 07/465,858, filed Jan. 16, 1990, now U.S. Pat. No. 5,084,466.

The present invention relates to new carboxamides and sulfonamides of the general formula $$R^1—A—(W)_a—X—(CH_2)_b—(Y)_c—B—Z—COOR \quad (I)$$

in which

A denotes a radical

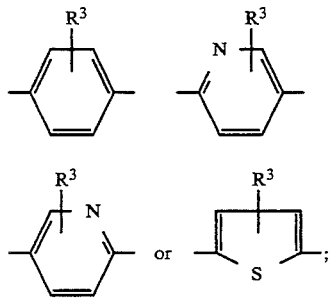

B denotes a radical

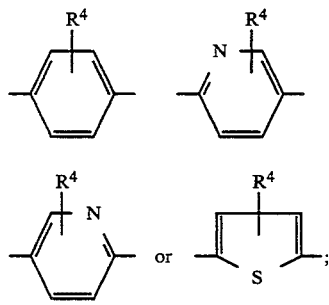

W denotes —$CH_2$—, —$CH_2CH_2$—, —CH=CH—, —CH=CH—$CH_2$—, —$(CH_2)_3$—, —$CH_2CH(CH_3)$—, —$COCH_2$—, —CH(OH)$CH_2$— or —$CH_2COCH_2$—;

X denotes —$CONR^2$—, $NR^2CO$—, —$SO_2NR^2$—or —$NR^2SO_2$—;

Y denotes —$CH_2CH_2$—, —$CH_2CH_2O$—, —$OCH_2$—, —$CH(CH_3)CH_2$—, —CH=CH—, —$CH_2$—CH=CH—, —$C(Q^1,Q^2)$—$CO(CH_2)_d$—, —$CH_2$—, —$CH_2CH_2CH_2$—, —$CH(CH_3)CH_2CH_2$—, —$CH_2COCH_2$—, —$C(Q^1, Q^2)$—CH(OH)—, —$C(Q^1,Q^2)$—$CH(SSCH_3)$—, —$CH(CH_2OH)CH_2$— or —$CH(COOR)CH_2$—, it being possible for carbonyl groups also to be in the form of oxime, oxime ether, ketal or thioketal or enol ether and hydroxyl groups to be in the form of lower alkyl ether, di(lower alkyl)amino-lower-alkyl ether or of ester of lower alkanecarboxylic acids Z denotes —$OCH_2$—, $NR^6CH_2$—, —$CH_2CH_2$—, —$CH(CH_3)CH_2$—, —$CH_2$—, —CH=CH— or —$C(CH_3)$=CH—;

R denotes hydrogen, lower alkyl, phenyl or phenyl-lower alkyl;

$Q^1$ and $Q^2$ are hydrogen or lower alkyl or form, together with the C atom to which they are bonded, a 3- to 6-membered saturated ring;

$R^1$ denotes amidino or guanidino;

$R^2$ denotes hydrogen, lower alkyl, phenyl-lower-alkyl, phenyl-lower-alkyl which is substituted in the phenyl moiety by amino, amidino or —COOR, or a radical —$CH_2COOR$ or —Y—B—Z—COOR;

$R^3$ denotes hydrogen, lower alkyl, lower alkoxy, halogen, lower carbalkoxy, amino, lower alkylamino, di-lower-alkylamino or amidino;

$R^4$ denotes hydrogen, lower alkyl, lower alkoxy, halogen, lower carbalkoxy, amino, lower alkylamino, di-lower-alkyl-amino or a radical —Z—COOR or —CH=CH$(CH_2)_n$COOR;

$R^6$ denotes hydrogen, lower alkyl or benzyl;

n denotes an integer of 0–4;

a, c and d denote 0 or 1;

b denotes an integer of 0–2, where a and b are 0 when c is 1, and c is 0 when a or b is different from 0;

and physiologically tolerated salts thereof.

These compounds prevent the development of blood platelet thrombi as discussed infra. They are thus useful in the prevention and treatment of thromboses, apoplexy, myocordial infarct, inflammations and arteriosclerosis. These compounds also inhibit metastasis and are thus useful as antitumor agents.

The invention also relates to a process for the preparation of these novel compounds, methods of using these compounds in therapy, and to pharmaceutical compositions containing these compounds.

As used herein, the term "lower" designates groups with 1–6 carbon atoms. Examples of lower alkyl groups as such or as the constituent of alkoxy or alkylamino are methyl, ethyl, propyl, isopropyl, n-butyl, sec-butyl or tert-butyl.

Examples of lower alkanecarboxylic acids with which the hydroxyl groups present, where appropriate, in Y can be esterified are acetic acid, propionic acid and butyric acid. Examples of ketal and thioketal groups are lower alkyl and lower alkylene ketals and thioketals such as dimethoxy, ethylenedioxy, dimethylthio and ethylenedithio groups. Examples of lower alkyl ethers are methyl and ethyl ethers. Examples of enol ether groups Y are the groups —CH=$C(OCH_3)_3$— and —$CH_2$—$C(OCH_3)$=CH—.

The compounds of the formula I can be solvated, in particular hydrated. The hydration can take place during the preparation process or gradually occur as a consequence of hygroscopic properties of an initially anhydrous compound of the formula I.

Examples of physiologically tolerated salts of the compounds of the formula I are salts with physiologically tolerated mineral acids such as hydrochloric acid, sulphuric acid or phosphoric acid, or with organic acids such as methanesulphonic acid, p-toluenesulphonic acid, acetic acid, trifluoroacetic acid, citric acid, fumaric acid, succinic acid or salicylic acid. The compounds of the formula I can also form salts with physiologically tolerated bases. Examples of salts of this type are alkali metal, alkaline earth metal, ammonium and alkylammonium salts such as Na, K, Ca or trimethylammonium salt. The compounds of the formula I can also be in the form of zwitterions.

The compounds of the formula I which contain one or more asymmetric C atoms can be in the form of enantiomers, diastereomers or mixtures thereof, for example racemates.

A subgroup of compounds of the formula I are the compounds of the formula

$$R^1—A—X—Y—B—Z—COOR \quad (Ia).$$

Another subgroup of compounds of the formula I are the compounds of the formula

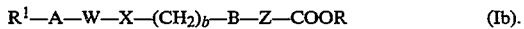

$$R^1—A—W—X—(CH_2)_b—B—Z—COOR \quad (Ib).$$

Preferred compounds of the general formula I are those in which the total of the C, O, N and S atoms present in (W)a, (CH$_2$)b, (Y)c, X and Z in a straight chain is 6.

Examples of such preferred compounds are compounds of the formula Ia, in which Y=—CH$_2$CH$_2$—, —CH$_2$CO—, —CH(CH$_3$)CO—, —CH(CH$_3$)CH(SSCH$_3$)—, —CH(CH$_3$)CH$_2$—, —CH═CH—, —CH$_2$CHOH— or —CH(COOR)CH$_2$—; and Z═—OCH$_2$—, —NR$^6$CH$_2$—, —CH$_2$CH$_2$—, —CH(CH$_3$)CH$_2$—, —CH═CH— or —C(CH$_3$)═CH—; or compounds of the formula Ib, in which W═—CH$_2$—, b=1 and Z is —OCH$_2$—, —NR$^6$CH$_2$—, —CH$_2$CH$_2$—, —CH(CH$_3$)CH$_2$—, —CH═CH—, or —C(CH$_3$)═CH—.

Also preferred are those compounds of general formula I in which R$^1$ is amidino, as well as those in which Y is —CH$_2$CH$_2$— or —CH$_2$CO—; Z is —OCH$_2$— or —CH$_2$CH$_2$— and X is —NHCO— or —CONH—. Additional preferred compounds include those in which R$^1$ is amidino and A and B are 1,4-C$_6$H$_4$; or R$^1$ is amidino, A is pyridyl and B is 1,4-C$_6$H$_4$; or R$^1$ is amidino, A is 1,4-C$_6$H$_4$ and B is 2,5-thienylen; or R$^1$ is guanidino and A and B are 1,4-C$_6$H$_4$. Additional preferred compounds include those in which R$^1$ is amidino, A and B are 1,4-C$_6$H$_4$, a and c are o, b is 2, X is —CON (Z-C$_6$H$_4$Z-K —COOCH$_3$)— and Z is —CH$_2$CH$_2$—.

R is preferably hydrogen.

The compounds of the general formula I and the salts thereof can be prepared according to the invention by the following process:

a) converting into an amido group the nitrile group in a compound of the general formula

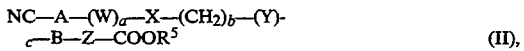

$$NC—A—(W)_a—X—(CH_2)_b—(Y)_c—B—Z—COOR^5 \quad (II),$$

in which R$^5$ is lower alkyl or benzyl, and A, B, W, X, Y, Z, a, b and c have the meaning specified above, and in which carboxyl groups which are present are in the form of esters; or b) eliminating the protective groups of the amidino or guanidino group from a compound of the general formula

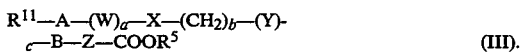

$$R^{11}—A—(W)_a—X—(CH_2)_b—(Y)_c—B—Z—COOR^5 \quad (III).$$

in which A, B, W, X, Y, Z, R$^5$, a, b and c have the meaning specified above, and R$^{11}$ represents a protected amidino or guanidino group; or c) converting into a guanidino group the amino group in a compound of the general formula

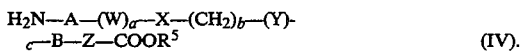

$$H_2N—A—(W)_a—X—(CH_2)_b—(Y)_c—B—Z—COOR^5 \quad (IV).$$

in which A, B, W, X, Y, Z, R$^5$, a, b and c have the meaning specified above, and in which the carboxyl groups which are present in the form of esters; or d) reacting a compound of the general formula

$$R^1—A—(W)_a—COE \quad (V),$$

in which E represents chlorine or bromine or COE represents an activated ester group, and R$^1$ A, W and a have the meaning specified above, with a compound of the general formula

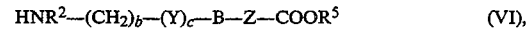

$$HNR^2—(CH_2)_b—(Y)_c—B—Z—COOR^5 \quad (VI),$$

in which Y, B, Z, R$^5$, R$^2$, b and c have the meaning specified above, and when R$^5$ is benzyl, it may be optionally eliminated.

It is further understood that the functional groups of compounds obtained by the above-described processes may have to be further modified according to standard techniques known in the art to yield specific compounds within general formula I.

The conversion of the nitrile group into the amidino group in process variant a) can be brought about by methods known per se, for example by reacting the nitrile with hydrogen sulfide and a base such as triethylamine in a solvent such as pyridine to give a thioamide, methylating the latter, for example with methyl iodide in acetone, and reacting the methylthioformimidoyl compound obtained in this way (that is to say a compound of the formula I in which the group —C(NH)SCH$_3$ is present in place of R$^1$) with ammonium acetate.

In process,variant b) amidino and guanidino groups can be protected by conventional protective groups such as benzyloxycarbonyl or tert.-butoxycarbonyl. Examples of groups R$^{11}$ are —C(NH)NH-CO-Obenzyl, —C(N-Boc)NH-Boc, —NHC(NH)NHNO$_2$ and —NHC(N-Boc)NH-Boc, where Boc stands for tert.butoxycarbonyl.

These protective groups can be eliminated in a manner known per se, for example by catalytic hydrogenation in the case of a benzyloxycarbonyl group or a nitro group, or by treatment with an acid such as trifluoroacetic acid in the case of a tert.butoxycarbonyl group.

The conversion of the amino group into the guanidino group as in process variant c) can be carried out by reaction with 2-S-isothiourea ethanesulphonate in the presence of a base such as Na$_2$CO$_3$ or NaOH at temperatures up to about 40° C.

Examples of activated ester groups COE in the compounds of the formula V are the p-nitrophenyl ester or the 4,6-dimethoxy-1,3,5-triazin-2-yl ester. The reaction of the activated ester V with the amine VI as in process variant d) can be carried out in a manner known per se in the presence of a base such as triethylamine, N-methylmorpholine or pyridine.

A benzyl ester group R$^5$ contained in the final process product can be eliminated in a manner known per se by hydrogenolysis, for example by hydrogenation in the presence of a noble metal catalyst such as Pd or PtO$_2$. Suitable as modification of functional groups in a compound of the formula I is hydrolysis of ester groups R$^5$ and of ester groups which may be present in the radicals R$^2$, R$^3$, R$^4$ and Y; the cleavage of ether or enol ether groups, ketal or thioketal groups which may be present in the radical Y; the hydrogenation of olefinic double bonds in the radical Y or Z; and the conversion of carboxylic acid groups into salts.

These modifications can be carried out in a manner known per se, for example by treatment with bases such as aqueous alcoholic NaOH to hydrolyze ester groups or by treatment with acids such as aqueous alcoholic hydrochloric acid to cleave ether and ketal groups, or by catalytic hydrogenation of a —C≡C— bond contained in Y or Z.

The starting compounds of the formulae II–VI can be prepared as described hereinafter:

An acid derivative of the general formulae $$R^x\text{—}A\text{—}(W)_a\text{—}COE \quad (VII),$$

or $$R^x\text{—}A\text{—}(W)_a\text{—}SO_2E \quad (VIII),$$

in which $R^x$ represents —CN, a group $R^{11}$ or a protected amino group and E represents an activated ester group or chlorine or bromine, can be reacted with an amine of the general formula $$HN(R^2)\text{—}(CH_2)_b\text{—}(Y)_c\text{—}B\text{—}Z\text{—}COOR^5 \quad (IX)$$

to give a compound of the formulae II, III or IV in which X represents a group —CONR²— or —SO₂NR².

Analogously, an acid derivative of the general formulae $$ECO\text{—}(CH_2)_b\text{—}(Y)_c\text{—}B\text{—}Z\text{—}COOR^5 \quad (X)$$

or $$ESO_2\text{—}(CH_2)_b\text{—}(Y)_c\text{—}B\text{—}Z\text{—}COOR^5 \quad (XI)$$

can be reacted with an amine of the general formula $$R^x\text{—}A\text{—}(W)_a\text{—}NHR^2 \quad (XII)$$

to give a compound of the formulae II, III or IV in which X represents a group —NR²CO— or —NR²SO₂—.

The condensation can be carried out in a manner known per se, for example by the method of activated esters or of mixed anhydrides or via the acid chlorides. For example, for the preparation of a compound VII or VIII, the corresponding acid is reacted with 2-chloro-4,6-dimethoxy-1,3,5-triazine in the presence of N-methylmorpholine to give an activated ester which can be reacted in situ with the amine IX. It is also possible to employ a p-nitrophenyl ester as activated ester. Mixed anhydrides can be obtained by reaction of the acid with isobutyl chloroformate. Alternatively, a halide of the formula VII or VIII can be reacted with an amine IX in the presence of a base such as triethylamine.

Where the reactants in groups A and B contain primary or secondary amino groups or carboxyl groups, it is expedient to protect these groups. An example of a suitable protective group for amino groups is tert.butoxycarbonyl. A carboxyl group can be protected by esterification, for example as alkyl ester. The introduction and removal of such groups can be carried out in a manner known per se.

A protected guanidino group, for example —NHC(N—Boc)—NH—Boc, can be constructed from an amino group by reacting the amine with N,N'-bis(t-butoxycarbonyl)-S-methylisothiourea in t-butanol, water and triethylamine.

Starting compounds VII or VIII with a protected amidino group can be prepared by converting an appropriate nitrile into the amidino, as described above for the compound II, and reacting the latter with a reagent providing the protective group. For example, a protected amidino group of the formula —C(NH)NH—CO—Obenzyl can be formed by reacting an amidino with benzyl chloroformate in the presence of triethylamine.

The compounds of the formula I, their solvates and their salts inhibit both the binding of fibrinogen, fibronectin and von Willebrand factor to the fibrinogen receptor of blood platelets (glycoprotein IIb/IIIa) and the binding thereof and other adhesive proteins, such as vitronectin, collagen and laminin, to the corresponding receptors on the surface of various types of cells. Hence the compounds according to the invention influence cell-cell and cell-matrix interactions. They prevent, in particular, the development of blood platelet thrombi and can be used in the control or prevention of diseases such as thrombosis, apoplexy, myocardial infarct, inflammations and arteriosclerosis. These compounds furthermore have an affect on tumor cells, in that they inhibit metastasis. Hence they can also be employed as antitumor agents.

The inhibition of fibrinogen binding to the fibrinogen receptor, glycoprotein IIb/IIIa, can be demonstrated as follows:

Glycoprotein IIb/IIIa is obtained from Triton X-100 extracts of human blood platelets and purified by lectin affinity chromatography (Analytical Biochemistry 151, 1985, 169–177) and chromatography on an Arg-Gly-Asp-Ser affinity column (Science 231, 1986, 1559–62). The receptor protein obtained in this way is bound to microtitre plates. The specific binding of fibrinogen to the immobilized receptor is determined using an ELISA system (enzyme-linked immunosorbent assay). The $IC_{50}$ values hereinafter correspond to that concentration of the test substance required to inhibit the binding of fibrinogen to the immobilized receptor by 50%:

| Product of Example: | 1 | 2 | 10 | 12 | 18 |
|---|---|---|---|---|---|
| $IC_{50}$ (μM) | 0.37 | 0.04 | 0.64 | 0.1 | 0.72 |
| Product of Example: | 20 | 36 | 40 | 46 | 48 | 78 |
| $IC_{50}$ (μM) | 0.47 | 0.1 | 0.04 | 0.3 | 0.03 | 0.97 |
| Product of Example: | 81 | 82 | 83 |
| $IC_{50}$ (μM) | 0.08 | 0.0081 | 0.00007 |

Pharmaceuticals containing a compound of the formula I, a solvate thereof or a salt thereof, can be administered enternally, for example orally in the form of tablets, lacquered tablets, sugar-coated tablets, hard and soft gelatin capsules, solutions, emulsions or suspensions, or rectally, for example in the form of suppositories, or as spray. However, administration can also take place parenterally, for example in the form of injectable solutions.

To prepare tablets, lacquered tablets, sugarcoated tablets and hard gelatin capsules, the active compound can be mixed with pharmaceutically inert, inorganic or organic excipients. Examples of such excipients which can be used for tablets, sugar-coated tablets and hard gelatin capsules are lactose, maize starch or derivatives thereof, talc, stearic acid or salts thereof. Examples of suitable excipients for soft gelatin capsules are vegetable oils, waxes, fats, semisolid and liquid polyols; however, no excipients whatever are necessary with soft gelatin capsules if the characteristics of the active compound are appropriate. Examples of suitable excipients for the preparation of solutions and syrups are water, polyols, sucrose, invert sugar and glucose, suitable examples for injectable solutions are water, alcohols, polyols, glycerol and vegetable oils, and suitable examples for suppositories are natural or hardened oils, waxes, fats and semiliquid or liquid polyols. The pharmaceutical products can additionally contain preservatives, solubilizers, stabilizers, wetting agents, emulsifiers, sweeteners, colorants, flavorings, salts to alter the osmotic pressure, buffers, coating agents or antioxidants.

The dosage of the active compound for controlling or preventing the diseases which were mentioned above can vary within wide limits and should, of course, be adjusted to suit the individual circumstances in each particular case as is understood in the art. In general, a dose of about 0.1 to 20 mg/kg, preferably of about 0.5 to 4 mg/kg, per day ought to be appropriate on oral administration for adults.

EXAMPLE 1

$H_2S$ was passed for 45 minutes through a suspension of 2.0 g of methyl 4-[2-(p-cyanobenzamido)ethyl]phenoxyacetate in 24 ml of pyridine/triethylamine (7:1) at 0° C. The solution resulting after 12 hours was concentrated, and a suspension was made of the residue in methanol and filtered. The residue on the filter was immediately suspended in 30 ml of acetone, and 4 ml of methyl iodide were added. After 2.5 hours the precipitate was filtered off, washed with a little acetone and, after drying, dissolved in 20 ml of methanol. 2.0 g of ammonium acetate were added and the mixture was then left to react at room temperature for 2 hours, during which a colorless precipitate formed, and this was filtered off and reprecipitated from methanol. Methyl p-[2-(p-amidinobenzamido)ethyl]phenoxyacetate was obtained as the acetate salt, melting point above 200° C., after drying under high vacuum.

Preparation of the starting material 1.12 ml of N-methylmorpholine were added to a suspension, cooled to 0° C., of 1.47 g of p-cyanobenzoic acid and 1.79 g of 2-chloro-4,6-dimethoxy-1,3,5-triazine in 40 ml of dichloromethane. After 3 hours at room temperature, the reaction mixture was cooled to 0° C., and a suspension of 2.45 g of methyl 4-(2-aminoethyl)-phenoxyacetate (prepared in analogy to the preparation of the ethyl ester described in German Offenlegungsschrift 2,809,377) and 1.1 ml of N-methylmorpholine in 40 ml of dichloromethane was added. The reaction mixture was stirred at room temperature overnight and subsequently concentrated. A suspension was made of the residue in ethyl acetate/water and filtered, and the filtrate was washed successively with 1 N hydrochloric acid, water, saturated sodium bicarbonate solution and water, dried over sodium sulphate and evaporated. A suspension of the residue was made in ether/dichloromethane/hexane and filtered, and the resulting methyl 4-[2-(p-cyanobenzamido)ethyl]phenoxyacetate, having a melting point of 149°–151° C., was dried.

EXAMPLE 2

A solution of 99 mg of sodium hydroxide in 1.5 ml of water was added to a suspension of 800 mg of the acetate salt of methyl p-[2-(p-amidinobenzamido)ethyl]phenoxyacetate in methanol. After 2 hours at 63° C., the reaction mixture was concentrated, the residue was suspended in 20 ml of water, and 822 mg of p-toluenesulphonic acid monohydrate were added to neutralize. The precipitate was filtered off, washed with a little water and dried under high vacuum, resulting in the p-toluenesulphonic acid salt of p-[2-(amidinobenzamido)ethyl]phenoxyacetic acid, melting point above 200° C.

EXAMPLE 3

In analogy to Example 1, the acetic acid salt of methyl 4-[2-(p-amidinobenzamido)ethyl]-2-iodophenoxyacetate, melting point 205°–206° C., was obtained from methyl 4-[2-(p-cyanobenzamido)ethyl]-2-iodophenoxyacetate.

The starting material was prepared as follows: A solution of 8.25 g of 4-cyanobenzoyl chloride in 25 ml of tetrahydrofuran was added dropwise to a suspension of 6.85 g of tyramine in 75 ml of tetrahydrofuran. Addition of 4 ml of pyridine resulted in the formation of a thick paste which, after 1 hour at room temperature, was concentrated. The residue was partitioned between ethyl acetate and 1 N hydrochloric acid, extracted twice with ethyl acetate, and the extract was washed with water, dried over sodium sulphate and evaporated. Trituration of the residue with methylene chloride resulted in 5.8 g of a colorless powder, which was suspended in 50 ml of acetic acid, and 6.5 g of iodine monochloride in 30 ml of acetic acid were added. After 3 hours at room temperature, the reaction mixture was concentrated and again triturated with methylene chloride. The precipitate which formed was filtered off with suction and dried. The residue was dissolved in 50 ml of dimethylformamide, 4.5 g of powdered potassium carbonate and 3.7 g of methyl bromoacetate were added, and the mixture was maintained at room temperature for 1 hour. The reaction mixture was then partitioned between ethyl acetate and 0.5 N hydrochloric acid, extracted with ethyl acetate and recrystallized from ethanol, resulting in methyl 4-[2-(p-cyanobenzamido)ethyl]-2-iodophenoxyacetate, melting point 160° C.

EXAMPLE 4

4-[2-(p-amidinobenzamido)ethyl]-2-iodophenoxyacetic acid, melting point above 250° C., was obtained from the acetic acid salt of methyl 4-[2-(p-amidinobenzamido) ethyl]-2-iodophenoxyacetate by treatment with aqueous methanolic sodium hydroxide solution at room temperature.

EXAMPLE 5

In analogy to Example 1, benzyl (E)-5-[5-[2-(p-amidino benzamido)ethyl]-2-carbomethoxymethoxyphenyl]-4-pentenoate (beige foam after chromatography on silica gel with dichloro-methane/methanol 19:1 to 4:1 as eluent) was obtained from benzyl (E)-5-[5-[2-(p-cyanobenzamido)ethyl]-2-carbomethoxymethoxyphenyl]-4-pentenoate by successive treatment with hydrogen sulphide, methyl iodide and ammonium acetate.

The starting material was prepared as follows:

A mixture of 464 mg of methyl 4-[2-(p-cyanobenzamido)ethyl]-2-iodophenoxyacetate, 2 ml of benzyl allylacetate, 5.2 mg of triphenylphosphine, 5.2 mg of palladium(II) acetate and 0.2 ml of triethylamine were heated at 100° C. under argon for 6 hours, with the same amounts of triethylamine, triphenylphosphine and palladium(II) acetate being added again after 5 hours. The mixture was then left to cool to room temperature and was diluted with dichloromethane. Chromatography on silica gel (eluent ether/petroleum ether 1:1) resulted in 480 mg of benzyl (E)-5-[5-[2-(p-cyanobenzamido)ethyl]-2-carbomethoxymethoxy phenyl]-4-pentenoate as a beige resin.

EXAMPLE 6

(E)-5-[5-[2-(p-Amidinobenzamido)ethyl]-2-carboxy methoxyphenyl]-4-pentenoic acid was obtained as monohydrate of melting point 247°–248° C. (from acetonitrile/water) by basic hydrolysis of benzyl (E)-5-[5-[2-(p-amidinobenzamido) ethyl]-2-carbomethoxymethoxyphenyl]-4-pentenoate in analogy to Example 2.

EXAMPLE 7

Methyl p-[2-(p-amidinobenzamido)ethoxy]phenylacetate was obtained as acetic acid salt of melting point 222°–223° C. (from ethanol) from methyl p-[2-(p-cyanobenzamido)ethoxy]phenylacetate in analogy to Example 1.

The starting material was prepared as follows:

1.66 g of methyl 4-hydroxyphenylacetate were reacted with 3.05 g of N-benzyloxycarbonyl-2-aminoethyl iodide in 30 ml of N,N-dimethylformamide in the presence of 2.8 g of potassium carbonate. After 2 hours at 100° C., the mixture was evaporated, the residue was partitioned between water and ether, and extraction with ether was carried out. Chromatography of the crude product resulted in 2.1 g of benzyl 2-(α-acetoxy-p-tolyloxy)ethylcarbamate as a colorless viscous oil.

A solution of 1 g of benzyl 2-(α-acetoxy-p-tolyloxy)ethylcarbamate in methanol was hydrogenated to saturation in the presence of 10% Pd/carbon. The residue obtained after filtration and evaporation was dissolved in chloroform, and 0.75 ml of triethylamine and 660 mg of 4-cyanobenzoyl chloride were added and the mixture was stirred for 30 minutes and then washed with 0.5 N sodium hydroxide solution, 0.5 N hydrochloric acid and water, dried and concentrated. The residue was recrystallized from ethyl acetate, resulting in 620 mg of methyl p-[2-(p-cyanobenzamido)ethoxy]phenylacetate, melting point 143°–144° C.

EXAMPLE 8

In analogy to Example 2, the p-toluenesulphonate of p-[2-(p-amidinobenzamido)ethoxy]phenylacetic acid, colorless needles of melting point 183°–184° C. (water/acetonitrile), were obtained from the acetic acid salt of methyl p-[2-(p-amidinobenzamido)ethoxy]phenylacetate.

EXAMPLE 9

In analogy to Example 1, the acetic acid salt of methyl p-[2-(p-amidinophenylsulphonamido)ethoxy]phenylacetate was obtained as colorless crystals of melting point 221°–222° C. (ethanol) from methyl p-[2-(p-cyanophenylsulphonamido)ethoxy]phenylacetate.

Preparation of the starting material

The starting material was obtained from benzyl 2-(α-acetoxy-p-tolyloxy)ethylcarbamate by hydrogenolysis of the benzyloxycarbonyl radical and subsequent reaction with 4-cyanobenzenesulphonyl chloride in the presence of triethylamine.

EXAMPLE 10

In analogy to Example 2, the p-toluenesulphonate of p-[2-(p-amidinophenylsulphonamido)ethoxy]phenylacetic acid was obtained as colorless crystals of melting point 210°–211° C. (from water) from the acetic acid salt of methyl p-[2-(p-amidinophenylsulphonamido)ethoxy]phenylacetate.

EXAMPLE 11

Hydrogen sulphide was passed for 60 minutes into a solution of 1.49 g of methyl p-[2-(p-cyanobenzenesulphonamido)ethyl]phenoxyacetate in 15 ml of pyridine and 1.5 ml of triethylamine at 0°–5° C. The reaction mixture was then maintained at room temperature overnight and subsequently evaporated to dryness in vacuo. 1.65 g of thioamide were obtained and were heated with 15 ml of methyl iodide in 15 ml of acetone under reflux for 3 hours. The reaction mixture was again evaporated in vacuo, and the residue was stirred with 1.30 g of ammonium acetate and 1.0 ml of acetic acid in 120 ml of chloroform at room temperature for 3 days. The residue obtained after the solvent had been evaporated off was dissolved in methanol/water and filtered through 30 g of Levafit M-5080. The filtrate was evaporated and chromatographed on 35 g of MCI gel with water/methanol (10:1). 1.0 g of pure, amorphous methyl p-[2-(p-amidinobenzenesulphonamido)ethyl]phenoxyacetate hydrochloride was obtained. IR bands (KBr) at 3117, 3053, 1756, 1681, 1512, 1333, 1228, 1155, 849 cm$^{-1}$.

The starting material was prepared as follows:

A solution of 1.21 g of p-cyanobenzenesulphonyl chloride in 20 ml of methylene chloride was added within 20 minutes to a stirred solution of 1.47 g of methyl 4-(2-aminoethyl)phenoxyacetate hydrochloride (melting point 190° C.) in 75 ml of methylene chloride and 1.85 ml of triethylamine at 0°–5° C. After stirring at room temperature for 2 hours, the usual working up was carried out, and the crude product was chromatographed on silica gel with chloroform/n-propanol/30% NH$_3$ (1000:10:1). Recrystallization of the TLC-pure fractions from acetone/hexane resulted in 1.95 g of pure methyl p-[2-(p-cyanobenzenesulphonamido)ethyl]phenoxyacetate as colorless needles, having a melting point of 148°–149° C.

EXAMPLE 12

A solution of 2.0 g of methyl p-[2-(p-amidinobenzenesulphonamido)ethyl]phenoxyacetate hydrochloride in 100 ml of ethanol and 50 ml of 1 N sodium hydroxide solution was stirred under argon for 90 minutes. For the working up, dilute hydrochloric acid was used to neutralize to pH 6–7, and the mixture was concentrated in vacuo up to 50° C. The crystals which separated out were filtered off with suction and dried over KOH in vacuo at 50° C. 1.70 g of pure p-[2-(p-amidinobenzenesulphonamido)ethyl]phenoxyacetic acid, melting point 292°–293° C., were thus isolated.

EXAMPLE 13

470 mg of methyl p-[(S)-2-(p-amidinobenzenesulphonamido) propyl]phenoxyacetate acetate of melting point 208°–210° C. (from methanol) were obtained as in Example 11 from 1.16 g of methyl p-[(S)-2-(p-cyanobenzenesulphonamido) propyl]phenoxyacetate.

The starting material was obtained by reaction of methyl p-[(S)-2-aminopropyl]phenoxyacetate hydrochloride (melting point 150°–152° C.) and p-cyanobenzenesulphonyl chloride in pyridine. Melting point 120°–122° C.

EXAMPLE 14

Pure amorphous p-[(S)-2-(p-amidinobenzenesulphonamido)propyl]phenoxyacetic acid hydrochloride was obtained as in Example 12, with subsequent treatment with one equivalent of hydrochloric acid, from methyl p-[(S)-2-(p-amidinobenzene sulphonamido)propyl]phenoxyacetate acetate (Example 13). IR bands (KBr) at 3342, 3102, 1680, 1609, 1510, 1324, 1206, 161, 847 cm$^{-1}$.

EXAMPLE 15

450 mg of pure amorphous methyl p-[2-(p-amidino-N-methyl-phenylsulphonamido)ethyl]phenoxyacetate hydrochloride were obtained as in Example 11 from 700 mg of methyl p-[2-(p-cyano-N-methylphenylsulphonamido)ethyl]phenoxyacetate. IR bands (KBr) at 3372, 3136, 3047, 1754, 1682, 1610, 1519, 1341, 1219, 1159, 828 cm$^{-1}$.

The starting material was prepared by reaction of methyl p-[2-(p-cyanobenzenesulphonamido)ethyl]phenoxyacetate (see Example 1) with butyllithium and methyl iodide in dimethoxyethane at room temperature. Melting point 82°–83° C.

EXAMPLE 16

Pure amorphous p-[2-(p-amidino-N-methylphenylsulphonamido)ethyl]phenoxyacetic acid hydrochloride was obtained as in Example 14 from methyl p-[2-(p-amidino-N-methylphenylsulphonamido)ethyl]phenoxyacetate hydrochloride (Example 15). IR bands (KBr) at 3277, 2942, 1692, 1609, 1512, 1421, 1335, 1227, 1156, 823 cm$^{1}$.

EXAMPLE 17

400 mg of pure amorphous methyl p-[-2-(p-amidino-N-benzylphenylsulphonamido)ethyl]phenoxyacetate hydrochloride were obtained as in Example 11 from 1.0 g of methyl p-[2-(p-cyano-N-benzylphenylsulphonamido)ethyl]phenoxyacetate. IR bands (KBr) at 3348, 3031, 1756, 1678, 1607, 1510, 1340, 1210, 1159, 852, 724, 697 cm$^{-1}$.

The starting material was obtained by reaction of methyl p-[2-(p-cyanobenzenesulphonamido)ethyl]phenoxyacetate (see Example 1) with butyllithium and benzylbromide in dimethoxyethane at room temperature. Melting point 108°–109° C. (from acetone/hexane).

EXAMPLE 18

240 mg of pure p-[2-(p-amidino-N-benzylphenylsulphonamido)ethyl]phenoxyacetic acid, melting point 275°–276° C. (decomposition), were obtained as in Example 12 from 340 mg of methyl p-[2-(p-amidino-N-benzylphenylsulphonamido)ethyl]phenoxyacetate hydrochloride (Example 17).

EXAMPLE 19

300 mg of pure methyl p-[2-(p-amidinobenzenesulphonamido)-1-hydroxyethyl)phenoxyacetate hydrochloride, melting point 227° C. (decomposition), were obtained as in Example 11 from 660 mg of methyl p-[2-(p-cyanobenzenesulphonamido)-1-hydroxyethyl]phenoxyacetate.

The starting material was obtained by reaction of methyl 4-(2-amino-1-hydroxyethyl)phenoxyacetate hydrochloride (melting point 123°–125° C.) and p-cyanobenzenesulphonyl chloride in pyridine. Melting point 126°–129° C. (from acetone/ether).

EXAMPLE 20

150 mg of pure amorphous p-[2-(p-amidinobenzenesulphonamido)-1-hydroxyethyl]phenoxyacetic acid were obtained as in Example 12 from 260 mg of methyl p-[2-(p-amidinobenzenesulphon-amido)-1-hydroxyethyl]phenoxyacetate hydrochloride (Example 19). IR bands (KBr) at 3431, 3036, 1688, 1608, 1572, 1511, 1419, 1321, 1152, 831 cm$^{1}$.

EXAMPLE 21

450 mg of pure methyl p-[2-(p-amidinobenzamido)-1-hydroxyethyl]phenoxyacetate hydrochloride of melting point 215°–218° C. were obtained as in Example 11 from 650 mg of methyl p-[2-(p-cyanobenzamido)-1-hydroxyethyl]phenoxyacetate.

The starting material was obtained by reaction of methyl 4-(2-amino-1-hydroxyethyl)phenoxyacetate hydrochloride (melting point 123°–125° C.) and p-cyanobenzoyl chloride in pyridine. Melting point 140°–142° C. (from acetone/hexane).

EXAMPLE 22

340 mg of pure p-[2-(p-amidinobenzamido)-1-hydroxyethyl]-phenoxyacetic acid, melting point above 250° C., were obtained as in Example 12 from 450 mg of methyl p-[2-(p-amidinobenzamido)-1-hydroxyethyl]phenoxyacetate hydrochloride.

EXAMPLE 23

250 mg of pure methyl p-(p-amidinophenylsulphonamidoacetyl)phenoxyacetate hydrochloride were obtained as a white powder as in Example 11 from 460 mg of methyl p-(p-cyanophenylsulphonamidoacetyl)phenoxyacetate. IR bands (KBr) at 3375, 3078, 1751, 1680, 1599, 1511, 1333, 1217, 1170, 832 cm$^{-1}$.

The starting material was obtained by oxidation of methyl p-[2-(p-cyanobenzenesulphonamido)-1-hydroxyethyl]phenoxyacetate with manganese dioxide in chloroform. Melting point 160°–162° C. (from acetone/hexane).

EXAMPLE 24

80 mg of pure crystalline p-(p-amidinophenylsulphonamidoacetyl)phenoxyacetic acid were obtained as in Example 12 from 180 mg of methyl p-(p-amidinophenylsulphonamidoacetyl)phenoxyacetate hydrochloride (Example 23). NMR bands at 2.49, 2.50, 3.30, 4.44(d), 4.35 ppm.

EXAMPLE 25

120 mg of pure crystalline methyl p-(p-amidinobenzamidoacetyl)phenoxyacetate hydrochloride, melting point 270°–271° C. (decomposition), were obtained as in Example 11 from 300 mg of methyl p-(p-cyanobenzamidoacetyl)phenoxyacetate.

The starting-material was obtained by oxidation of methyl p-[2-(p-cyanobenzamido)-1-hydroxyethyl]phenoxyacetate with manganese dioxide in chloroform. Melting point 200°–203° C.

EXAMPLE 26

A mixture of 80 mg of methyl p-(p-amidinobenzamidoacetyl)phenoxyacetate (Example 25), 40 mg of potassium carbonate, 10 ml of ethanol and 4 ml of water was stirred at room temperature under argon for 4 hours. 10 ml of water were then added to the mixture, which was neutralized to pH 6 with 1 N HCl. It was concentrated to 10 ml in vacuo and left to stand in a refrigerator overnight. The precipitate which had separated out was filtered off with suction and dried over KOH in vacuo at 50° C. 52 mg of amorphous p-(p-amidinobenzamidoacetyl)phenoxyacetic acid were obtained, IR bands (KBr) at 3354, 3286, 3042, 1647, 1598, 1542, 1485, 1422, 1360, 1232, 1177, 994 and 710 cm$^1$.

EXAMPLE 27

170 mg of pure methyl p-[2-[p-amidino-N-(p-carbomethoxybenzyl)phenylsulphonamido]ethyl]phenoxyacetate hydrochloride were obtained as in Example 11 from 300 mg of methyl p-[2-[p-cyano-N-(p-carbomethoxybenzyl)phenylsulphonamido]ethyl]phenoxyacetate. IR bands (KBr) at 3380, 2952, 1757, 1719, 1684, 1611, 1511, 1285, 1210, 1156, 586 cm$^{-1}$.

The starting material was obtained by reaction of methyl p-[2-(p-cyanobenzenesulphonamido)ethyl]-phenoxyacetate (see Example 1) with butyllithium and p-carbomethoxybenzylbromide in dimethoxyethane at room temperature. Melting point 118°–119° C. (from acetone/hexane).

EXAMPLE 28

84 mg of pure amorphous p-[2-[p-amidino-N-(p-carboxybenzyl)phenylsulphonamido]ethyl]phenoxyacetic acid were obtained as in Example 12 from 150 mg of methyl p-[-2-[p-amidino-N-(p-carbomethoxybenzyl)-phenylsulphonamido]ethyl]phenoxyacetate hydrochloride (Example 27). IR bands (KBr) at 381, 2930, 1689, 1609, 1546, 1511, 1386, 1335, 1156, 823, 592 cm$^{-1}$.

EXAMPLE 29

1.3 g of pure dimethyl [4-[2-(p-amidinophenylsulphonamido)ethyl]-o-phenylenedioxy]diacetate hydrochloride were obtained as a white amorphous powder as in Example 11 from 2.31 g of dimethyl [4-[2-(p-cyanophenylsulphonamido)ethyl]-o-phenylenedioxy]diacetate. IR bands (KBr) at 3351, 3087, 2857, 1759, 1680, 1596, 1515, 1479, 1330, 1218, 1156, 850 cm$^{-1}$.

The starting material was obtained by reaction of dimethyl 3,4-(2-aminoethyl)phenylene-dioxy-diacetate with p-cyanobenzenesulphonyl chloride in pyridine, melting point 130°–131° C. (from acetone/hexane).

EXAMPLE 30

400 mg of pure crystalline [4-[2-(p-amidinophenylsulphonamido)ethyl]-o-phenylenedioxy]diacetic acid of melting point 203°–205° C. were obtained as in Example 12 from 500 mg of dimethyl[4-[2-(p-amidinophenylsulphonamido)ethyl]-o-phenylenedioxy]diacetate hydrochloride.

EXAMPLE 31

830 mg of pure amorphous methyl 4-[2-(p-amidinophenyl sulphonamido)ethyl]-2-methoxyphenoxyacetate hydrochloride were obtained as in Example 11 from 960 mg of methyl 4-[2-(p-cyanophenylsulphonamido)ethyl]-2-methoxyphenoxyacetate. IR bands (KBr) at 3365, 3091, 1749, 1681, 1605, 1515, 1329, 1262, 1219, 1151, 850, 806 cm$^{-1}$.

The starting material was obtained by reaction of methyl 4-(2-aminoethyl)-2-methoxyphenoxyacetate hydrochloride (melting point 152°–154° C.) and p-cyanobenzenesulphonyl chloride in pyridine, melting point 132°–133° C.

EXAMPLE 32

570 mg of pure crystalline 4-[2-(p-amidinophenylsulphonamido)ethyl]-2-methoxyphenoxyacetic acid of melting point 190°–192° C. (decomposition) were obtained as in Example 12 from 770 mg of methyl 4-[2-(p-amidinophenylsulphonamido)ethyl]-2-methoxyphenoxyacetate hydrochloride (Example 31).

EXAMPLE 33

0.80 g of pure amorphous methyl (E)-p-[2-(p-amidinophenylsulphonamido)ethyl]-$\beta$-methyl-cinnamate hydrochloride was obtained as in Example 11 from 1.0 g of methyl (E)-p-[2-(p-cyanophenylsulphonamido)ethyl]-$\beta$-methylcinnamate.

The starting material was obtained by reaction of methyl-4-(2-aminoethyl)-$\beta$-methyl-cinnamate hydrochloride (melting point 197°–199° ) and p-cyanobenzenesulphonyl chloride in pyridine, melting point 118°–120° C.

EXAMPLE 34

140 mg of pure amorphous (E)-p-[2-(p-amidinophenylsulphonamido)ethyl]-$\beta$-methyl-cinnamic acid were obtained as in Example 12, but extending the reaction time to 24 hours, from 300 mg of methyl (E)-p-[2-(p-amidinophenylsulphonamido)ethyl]-$\beta$-methyl-cinnamate hydrochloride. IR bands (KBr) at 3393, 2926, 1698, 1627, 1556, 1479, 1385, 1329, 1246, 1156, 1093, 832, 597 cm$^{-1}$.

EXAMPLE 35

300 mg of methyl (E)-p-[2-(p-amidinophenylsulphonamido)ethyl]-$\beta$-methyl-cinnamate hydrochloride were dissolved in 40 ml of methanol and 40 ml of acetic acid and, after addition of 300 mg of 10% Pd/C catalyst, hydrogenated under atmospheric pressure and at room temperature until 1 equivalent of hydrogen had been absorbed. Removal of the catalyst by filtration and evaporation of the solvent resulted in 273 mg of amorphous methyl p-[2-(p-amidinophenylsulphonamido)ethyl]-$\beta$-methyl-hydrocinnamate hydrochloride.

EXAMPLE 36

120 mg of pure crystalline p-[2-(p-amidinophenylsulphonamido)ethyl]-$\beta$-methyl-hydrocinnamic acid, melting point above 200° C., were obtained as in Example 12, but extending the reaction time to 4 hours, from 200 mg of methyl p-[2-(p-amidinophenylsulphonamido)ethyl]-$\beta$-methylhydrocinnamate hydrochloride.

EXAMPLE 37

2.3 g of amorphous ethyl (E)-5-[(RS)-2-(p-amidinobenzamido)propyl]-$\beta$-methyl-2-thiopheneacrylate hydrochloride were obtained as in Example 11 from 3.70 g of ethyl (E)-5-[(RS)-2-(p-cyanobenzamido)-propyl]-$\beta$-methyl-2-thiophene-acrylate hydrochloride. IR Bands (KBr) at 3254, 3057, 1700, 1679, 1638, 1611, 1541, 1485, 1290, 1164, 861, 712 cm$^{-1}$.

The starting material was prepared by reaction of ethyl (E)-5-[(RS)-2-aminopropyl]-$\beta$-methyl-2-thiophene-acrylate with p-cyanobenzoyl chloride in pyridine, melting point 153°–154° C. (from acetone/hexane).

EXAMPLE 38

220 mg of pure (E)-5-[(RS)-2-(p-amidinobenzamido)propyl]-β-methyl-2-thiophene-acrylic acid were obtained as in Example 34 from 435 mg of ethyl (E)-5-[(RS)-2-(p-amidinobenzamido)propyl]-β-methyl-2-thiophene-acrylate hydrochloride (Example 37). Melting point above 230° C.

EXAMPLE 39

360 mg of pure crystalline ethyl (RS)-5-[(RS)-2-(p-amidinobenzamido)propyl]-β-methyl-2-thiophene-propionate hydrochloride were obtained as in Example 35 from 700 mg of ethyl (E)-5-[(RS)-2-(p-amidinobenzamido)propyl]-β-methyl-2-thiophene-acrylate hydrochloride. IR bands (KBr) at 3397, 2929, 1733, 1680, 1636, 1548, 1485, 1278, 1021, 864 cm$^{-1}$.

EXAMPLE 40

260 mg of colorless amorphous (RS)-5-[(RS)-2-(p-amidinobenzamido)propyl]-β-methyl-2-thiophene-propionic acid were obtained as in Example 12 from 320 mg of ethyl (RS)-5-[(RS)-2-(p-amidinobenzamido)propyl]-β-methyl-2-thiophene-propionate hydrochloride (Example 39). IR bands (KBr) at 3262, 2928, 1633, 1557, 1499, 1401, 1155, 869, 698 cm$^-$.

EXAMPLE 41

530 mg of pure methyl p-[2-(p-amidinobenzamido)ethyl]hydrocinnamate hydrochloride were obtained as in Example 11 from 770 mg of methyl p-[2-(p-cyanobenzamido)ethyl]hydrocinnamate. IR bands (KBr) at 3297, 3088, 1735, 1682, 1633, 1548, 1487, 1295, 1172, 864 cm$^{-1}$.

The starting material was obtained by reaction of methyl-4-(2-aminoethyl)hydrocinnamate hydrochloride with p-cyanobenzoyl chloride in methylene chloride in the presence of triethylamine. Melting point 142°–144° C.

EXAMPLE 42

430 mg of pure crystalline p-[2-(p-amidinobenzamido) ethyl]-hydrocinnamic acid, melting point above 230° C., were obtained as in Example 12 from 490 mg of methyl p-[-2-(p-amidinobenzamido)-ethyl]hydrocinnamate hydrochloride.

EXAMPLE 43

0.75 g of pure methyl p-[3-(p-amidinobenzamido)propyl]phenylacetate hydrochloride was obtained as in Example 11 from 1.0 g of methyl p-[3-(p-cyanobenzamido)propyl]phenylacetate hydrochloride. IR bands (KBr) at 3261, 3059, 1734, 1680, 1638, 1545, 1484, 1436, 1155, 1014, 863 cm$^{-1}$.

The starting material was obtained by reaction of methyl-4-(3-aminopropyl)phenylacetate hydrochloride (melting point 168°–171° C.) with p-cyanobenzoyl chloride in methylene chloride and in the presence of triethylamine. Melting point 122°–124° C. (from acetone/hexane).

EXAMPLE 44

420 mg of p-[3-(p-amidinobenzamido)propyl]phenylacetic acid hydrochloride were obtained as an amorphous powder as in Example 12, with subsequent conversion into the hydrochloride with HCl, from 650 mg of methyl p-[3-(p-amidinobenzamido)propyl]phenylacetate hydrochloride. IR bands (KBr) at 3498, 2923, 1670, 1643, 1545, 1517, 1389, 1280, 1136, 839, 707 cm$^{-1}$.

EXAMPLE 45

510 mg of pure amorphous methyl p-[3-(p-amidinophenylsulphonamido)propyl]phenylacetate hydrochloride were obtained as in Example 11 from 1.0 g of methyl p-[3-(p-cyanophenylsulphonamido)propyl]phenylacetate. IR bands (KBr) at 3420, 3257, 3105, 1718, 1659, 1775, 1520, 1477, 1339, 1227, 1152, 851, 806 cm$^{-1}$.

The starting material was obtained by reaction of methyl-4-(3-aminopropyl)phenylacetate hydrochloride (melting point 168°–171°) with p-cyanobenzenesulphonyl chloride in methylene chloride and in the presence of triethylamine. Melting point 149°–151° C. (acetone/hexane).

EXAMPLE 46

340 mg of pure crystalline p-[3-(p-amidinophenylsulphonamido)propyl]phenylacetic acid, melting point above 250° C., were obtained as in Example 12 from 510 mg of methyl p-[3-(p-amidinophenylsulphonamido)propyl]phenylacetate hydrochloride (Example 45).

EXAMPLE 47

890 mg of pure amorphous methyl p-[2-(4-amidino-3-pyridylamido)ethyl]phenoxyacetate hydrochloride were obtained as in Example 11 from 1.0 g of methyl p-[2-(4-cyano-3-pyridylamido)ethyl]phenoxyacetate. IR bands (KBr) at 3430, 3242, 3063, 1762, 1695, 1643, 1515, 1437, 1215, 1081 cm$^{-1}$.

The starting material was obtained by reaction of 6-cyanonicotinic acid (melting point 184°–186°) with ethyl chloroformate in the presence of 4-ethylmorpholine and subsequent reaction with methyl 4-(2-aminoethyl)-phenoxyacetate hydrochloride in tetrahydrofuran. Melting point 147°–149° C. (from acetone/hexane).

EXAMPLE 48

625 mg of pure crystalline p-[2-(4-amidino-3-pyridylamido)ethyl]phenoxyacetic acid were obtained as in Example 12 from 800 mg of methyl p-[2-(4-amidino-3-pyridylamido)ethyl]phenoxyacetate hydrochloride (Example 47). Melting point >200° C.

EXAMPLE 49

220 mg of pure amorphous dimethyl p,p'-[(p-amidinobenzoyl-imino)diethylene]-dihydrocinnamate hydrochloride were obtained as in Example 11 from 530 mg of dimethyl p,p'-[(p-cyanobenzoylimino)diethylene]-dihydrocinnamate. IR bands (KBr) at 3010, 2945, 1794, 1682, 1612, 1514, 1495, 1205, 1018, 851 cm$^{-1}$.

The starting material was obtained by reaction of p-cyanobenzoyl chloride with dimethyl N,N-bis-[4-(2-aminoethyl)]dihydrocinnamate. The latter was obtained by catalytic hydrogenation of methyl 4-(2-nitroethylene) cinnamate in methanol/Pd/C.

EXAMPLE 50

115 mg of pure crystalline p,p'-[(p'-amidinobenzoylimino)diethylene]-dihydrocinnamic acid, melting point >220° C., were obtained as in Example 12 from 210 mg of dimethyl p,p'-[(p-amidinobenzoylimino)diethylene]dihydrocinnamate hydrochloride.

EXAMPLE 51

600 mg of crystalline methyl p-[2-(p-amidinophenylcarbamoyl)ethyl]phenoxyacetate hydrochloride were obtained as in Example 11 from 940 mg of methyl p-[2-(p-cyanophenylcarbamoyl)ethyl]phenoxyacetate. Melting point 230°–232° C.

The starting material was obtained by reaction of 3-(4-hydroxyphenyl)propionic acid with ethyl chloroformate, 4-ethylmorpholine and p-aminobenzonitrile to give p-[2-(p-cyanophenylcarbamoyl)ethyl]phenol (melting point 169°–172° C.) and subsequent etherification with methyl bromoacetate/KOH in acetone. Melting point 140°–143° C. (from acetone/hexane).

EXAMPLE 52

450 mg of p-[2-(p-amidinophenylcarbamoyl)ethyl]-phenoxyacetic acid were obtained as in Example 12 from 570 mg of methyl p-[2-(p-amidinophenylcarbamoyl)ethyl]phenoxyacetate hydrochloride. Melting point >250° C.

EXAMPLE 53

0.8 g of pure amorphous methyl α-(p-amidinobenzylcarbamoyl)-p-tolyloxyacetate hydrochloride were obtained as in Example 11 from 1.02 g of methyl α-(p-cyanobenzylcarbamoyl)-p-tolyloxyacetate. IR bands (KBr) at 3376, 3263, 3060, 1751, 1654, 1612, 1511, 1180, 1080 cm$^{-1}$.

The starting material was prepared by reaction of 4-hydroxyphenylacetic acid with ethyl chloroformate/4-ethylmorpholine and then p-cyanobenzylamine to give p-(p-cyanobenzylcarbamoylmethyl)phenol (melting point 176°–178° C.) and subsequent etherification with methyl bromoacetate/KOH in acetone. Melting point 143°–145° C. (from acetone/hexane). IR bands (KBr) at 3284, 3034, 2232, 1747, 1637, 1610, 1536, 1509, 1374, 1219, 1093, 810 cm$^{-1}$.

EXAMPLE 54

305 mg of amorphous α-(p-amidinobenzylcarbamoyl)-p-tolyloxy acetic acid were obtained as in Example 12 from 391 mg of methyl α-(p-amidinobenzylcarbamoyl)-p-tolyloxyacetate hydrochloride. IR bands (KBr) at 3289, 3044, 1697, 1651, 1612, 1409, 1249, 1222, 1057, 850, 775 cm$^{-1}$.

EXAMPLE 55

322 mg of pure amorphous methyl p-(p-amidinophenethyl carbamoyl)phenoxyacetate hydrochloride were obtained as in Example 11 from 400 mg of methyl p-(p-cyanophenethylcarbamoyl)phenoxyacetate. IR bands (KBr) at 3400, 3175, 1755, 1694, 1640, 1608, 1550, 1509, 1435, 1294, 1086, 764 cm$^{-1}$.

The starting material was prepared by reaction of 4-hydroxybenzoic acid with ethyl chloroformate/4-ethylmorpholine and subsequent addition of p-cyanophenethylamine to give p-(p-cyanophenethylcarbamoyl)phenol and then etherification with methyl bromoacetate/KOH in acetone.

EXAMPLE 56

190 mg of colorless amorphous p-(p-amidinophenethyl carbamoyl)phenoxyacetic acid were obtained as in Example 12 from 260 mg of methyl p-(p-amidinophenethylcarbamoyl)phenoxyacetate hydrochloride. IR bands (KBr) at 3373, 3057, 1694, 1638, 1608, 1575, 1542, 1500, 1409, 1313, 1227, 1179, 1055, 766 cm$^{-1}$.

EXAMPLE 57

0.9 g of pure amorphous methyl p-[2-(p-amidinobenzamido)-1-hydroxy-ethyl]hydrocinnamate hydrochloride was obtained as in Example 11 from 1.0 g of methyl p-[2-(p-cyanobenzamido)-1-hydroxy-ethyl]hydrocinnamate. IR bands (KBr) at 3294, 3087, 1729, 1682, 1641, 1545, 1483, 1292, 863 cm$^{-1}$.

The starting material was obtained by reaction of methyl 4-(2-amino-1-hydroxyethyl)hydrocinnamate hydrochloride (melting point 141°–144° C.) and p-cyanobenzoyl chloride in methylene chloride/triethylamine. Melting point 139°–141° C. (from acetone/hexane). IR bands (KBr) at 3324, 2237, 1736, 1644, 1549, 1501, 1293, 1170, 841 cm$^{-1}$.

EXAMPLE 58

690 mg of pure p-[2-(p-amidinobenzamido)-1-hydroxyethyl]hydrocinnamic acid were obtained as in Example 12 from 920 mg of methyl p-[2-(p-amidinobenzamido)-1-hydroxyethyl]hydrocinnamate hydrochloride. Melting point >250° C.

EXAMPLE 59

1.41 g of colorless amorphous methyl p-(p-amidinobenzamidoacetyl)hydrocinnamate hydrochloride were obtained as in Example 11 from 2.1 g of methyl p-(p-cyanobenzamidoacetyl)hydrocinnamate. IR bands (KBr) at 3371, 3045, 1737, 1680, 1650, 1605, 1538, 1484, 1229, 864 cm$^{-1}$.

The starting material was obtained by oxidation of methyl p-[2-(p-cyanobenzamido)-1-hydroxyethyl]hydrocinnamate (see Example 47) with manganese dioxide in chloroform. Melting point 160°–161° C. (from acetone/hexane).

EXAMPLE 60

100 mg of methyl p-(p-amidinobenzamidoacetyl)hydrocinnamate hydrochloride were heated with 4 ml of 2 N hydrochloric acid at 100° C. for 60 minutes. The reaction mixture was cooled, 4 ml of water were added, and the mixture was stirred at 5° C. for 2 hours. The crystals which precipitated was filtered off with suction and dried over KOH in vacuo. 70 mg of pure p-(p-amidinobenzamidoacetyl)hydrocinnamic acid hydrochloride, melting point 273°–274° C. (decomposition), were obtained.

EXAMPLE 61

A mixture of 486 mg of methyl 4-(2-aminoethyl)hydrocinnamate hydrochloride, 672 mg of 4-nitrophenyl-4-guanidino-benzoate hydrochloride, 404 mg of triethylamine and 10 ml of dimethylformamide was stirred at room temperature under argon for 5 hours. The reaction mixture was then evaporated to dryness in vacuo, and the residue was chromatographed on 25 g of MCI gel. 520 mg of amorphous methyl p-[2-(p-guanidinobenzamido)ethyl]hydrocinnamate hydrochloride were obtained. IR bands (KBr) at 3339, 3187, 1727, 1678, 1644, 1579, 1500, 1289, 1107, 852 cm$^{-1}$.

EXAMPLE 62

220 mg of p-[2-(p-guanidinobenzamido)ethyl]hydrocinnamic acid were obtained as an amorphous powder as in Example 11 from 450 mg of methyl p-[2-(p-guanidinobenzamido)ethyl]hydrocinnamate hydrochloride. IR bands (Nujol) at 3507, 3454, 3308, 2925, 1704, 1638, 1554, 1505, 1481, 1376, 1312, 865, cm$^{-1}$.

EXAMPLE 63

310 mg of pure amorphous methyl α-(p-guanidinobenzamido)-p-tolyloxy-acetate hydrochloride were isolated as in Example 61 from 231 mg of methyl p-aminomethylphenoxyacetate hydrochloride and 336 mg of 4-nitrophenyl-4-guanidino-benzoate hydrochloride. IR bands (KBr) at 3304, 3169, 1749, 1675, 1641, 1602, 1568, 1507, 1435, 1207, 1080 cm$^{-1}$.

EXAMPLE 64

181 mg of colorless amorphous α-(p-guanidinobenzamido)-p-tolyloxy-acetic acid hydrochloride were obtained as in Example 14 from 255 mg of methyl α-(p-guanidinobenzamido)-p-tolyloxy-acetate hydrochloride. IR bands (KBr) at 3285, 2538, 1674, 1622, 1509, 1419, 1252, 1176, 852, 699 cm$^{-1}$.

EXAMPLE 65

168 mg of pure amorphous methyl p-(p-guanidinobenzamidomethyl)hydrocinnamate hydrochloride were obtained as in Example 61 from 193 mg of methyl 4-aminomethylhydrocinnamate and 336 mg of 4-nitrophenyl 4-guanidino-benzoate. IR bands (KBr) at 3367, 2946, 1691, 1601, 1544, 1366, 1252, 1170, 1126, 961 cm$^{-1}$.

EXAMPLE 66

75 mg of colorless amorphous p-(p-guanidinobenzamidomethyl)hydrocinnamic acid hydrochloride were obtained as in Example 14 from 137 mg of methyl p-(p-guanidinobenzamidomethyl)hydrocinnamate hydrochloride. IR bands (KBr) at 3304, 3129, 1703, 1668, 1626, 1567, 1503, 1285, 827 cm$^{-1}$.

EXAMPLE 67

A solution of 200 mg of methyl α-(p-amidinohydrocinnamamido)-p-tolyloxyacetate hydroiodide (5:4) in 10 ml of methanol and 0.5 ml of 1 N sodium hydroxide solution was stirred at room temperature for 2 hours and, after addition of a further portion of 0.5 ml of 1 N sodium hydroxide solution, for another 2 hours. 2 ml of H$_2$O were added and then the solvent was removed by evaporation, and the remaining aqueous solution was adjusted to pH 2 with 1 M KHSO$_4$ solution and extracted with ethyl acetate. Removal of insolubles by filtration and purification of the residue from the organic phase by chromatography (reverse phase) on Merck RP18 octadecyl-derivatized silica gel with H$_2$O as eluent resulted in 77 mg of α-(p-amidinohydrocinnamamido)-p-tolyloxyacetic acid as a white powder of melting point 180° C. (decomposition).

The ester which was employed as starting material was prepared in the following manner:

A. 404 mg of N-methylmorpholine and 758 mg of O-benzotriazolyl-N,N,N,N-tetramethyluronium hexafluorophosphate were added to a stirred suspension of 350 mg of p-cyanohydrocinnamic acid and 463 mg of methyl p-aminomethylphenoxyacetate HCl in 20 ml of DMF/THF (1:1) while cooling to 0° C. After a reaction time of 90 minutes at room temperature, the mixture was evaporated to dryness under high vacuum, the oily residue was dissolved in ethyl acetate, and this solution was washed with 5% NaHCO$_3$, H$_2$O, 2M KHSO$_4$ and saturated NaCl solution. The crude product obtainable from the organic phase was purified by chromatography on silica gel with ethyl acetate as eluent and recrystallized from ethyl acetate/hexane: 630 mg of methyl α-(p-cyanohydrocinnamamido)-p-tolyloxyacetate, melting point 125° C.

B. A solution of 585 mg of the product from Step A in 60 ml of pyridine and 4 ml of triethylamine was saturated with H$_2$S at room temperature and stored at this temperature overnight. The residue from evaporation in a rotary evaporator was taken up in H$_2$O and extracted with ethyl acetate. The crude oily product was purified by chromatography on silica gel with ethyl acetate/MeOH (99:1 v/v) as eluent. Yield: 560 mg of methyl α-(p-thiocarbamoylhydrocinnamamido)-p-tolyloxyacetate, melting point 135° C.

C. 560 mg of thioamide of the product from Step B were dissolved in 50 ml of acetone, 2 ml of methyl iodide were added, and the mixture was heated under reflux for 45 minutes. The crude methyl α-(p-methylthiocarboximidohydrocinnamamido)-p-tolyloxyacetate hydriodide obtainable after evaporation of the solvent in a rotary evaporator was employed without further purification in the next stage. 125 mg of AcONH$_4$ were added to a solution of 575 mg of the precursor in 40 ml of MeOH, and the mixture was heated under reflux for 6 hours. The residue remaining after evaporation of the solvent in a rotary evaporator was induced to crystallize with ethyl acetate/hexane. Yield: 401 mg of methyl α-(p-amidinohydrocinnamamido)-p-tolyloxyacetate hydriodide (5:4), melting point 155° C., MS (FAB): 370 (M+H)$^+$.

EXAMPLE 68

In analogy to Example 67, p-(p-amidinohydrocinnamamido) phenoxyacetic acid, melting point >300° C. (water), was obtained on hydrolysis of methyl p-(p-amidinohydrocinnamamido)phenoxyacetate hydriodide (1:1).

The ester employed as starting material was prepared in the following manner:

A. In analogy to Example 67, Step A, methyl p-(p-cyanohydrocinnamamido)phenoxyacetate, melting point 141° C. (ethyl acetate/hexane) was obtained by coupling p-cyanohydrocinnamic acid and methyl p-aminophenoxyacetate HCl and from it, in analogy to Example 67, Step B, methyl p-(p-thiocarbamoylhydrocinnamamido)phenoxyacetate, melting point 80° C. (ethyl acetate), by thionation, and methylation with methyl iodide provides methyl p-[p-(1-methylthioformimidoyl)hydrocinnamamido)phenoxyacetate hydrodide, melting point 189° C. (acetone), from which methyl p-(p-amidinohydrocinnamamido)phenoxyacetate hydriodide, melting point 203°–205° C. (ethyl acetate/hexane) was obtained by ammonolysis.

EXAMPLE 69

120 mg of methyl p-((E)-p-amidinocinnamamido)-phenoxyacetate were heated in 12 ml of concentrated HCl, while passing in argon, under reflux and the mixture is filtered while still hot. The resulting p-((E)-p-amidinocinnamamido)phenoxyacetic acid hydrochloride was washed with a little concentrated HCl and hexane and dried over KOH in vacuo at 40° C. Yellow crystals, melting point 290° C. (decomposition).

The starting material was prepared in the following way:

A. In analogy to Example 67, section A., methyl p-((E)-p-cyanocinnamamido)phenoxyacetate was obtained by coupling p-cyanocinnamic acid and methyl p-aminophenoxyacetate HCl. Yellow crystals, melting point 197° C. (ethyl acetate/hexane).

B. 1.52 g of product from Step A above were suspended in 106 ml of dioxane, 2 ml of ether and 0.42 g of methanol were added, and the mixture was cooled to 5° C. While stirring vigorously, 1.40 g of gaseous hydrogen chloride were passed in at this temperature. The stirring and cooling were continued for 3 additional hours. Stirring was continued at room temperature over the weekend, and the insolubles were subsequently removed by filtration, washed with ether and dried in vacuo.

209 mg of this product were suspended in 50 ml of EtOH, and the mixture was cooled to 5° C. Ethanolic $NH_3$ solution (9 g/100 ml) was added to this until a distinct $NH_3$ excess was present. The stirred mixture was heated at 70° C. overnight and insolubles were removed by filtration while still hot. The solvent is evaporated to about 5 ml in a rotary evaporator, and the methyl p-[(E)-p-amidinocinnamamido]phenoxyacetate was induced to crystallize by addition of hexane. Yellow crystals, melting point above 235° C. Yield: 136 mg (68% of theory).

EXAMPLE 70

In analogy to Example 1, N-(p-amidinobenzoyl)-3-[p-(tert-butoxycarbonylmethoxy)phenyl]-D-alanine methyl ester is obtained as a pale yellow foam from N-(p-cyanobenzoyl)-3-[p-(tert-butoxycarbonylmethoxy)phenyl]-D-alanine methyl ester.

The starting material was prepared as follows:

(R)-N-benzyloxycarbonyl-tyrosine methyl ester was reacted in a manner analogous to that described in Example 3 with t-butyl bromoacetate in the presence of potassium carbonate to give N-benzyloxycarbonyl-3-[p-(tert-butoxycarbonylmethoxy)phenyl]-D-alanine methyl ester. The colorless oil was hydrogenated in methanol, after addition of 5% palladium/carbon, in a shaking apparatus at room temperature under atmospheric pressure, obtaining, after filtration and removal of the solvent, 3-[p-(tert-butoxycarbonylmethoxy)-phenyl]-D-alanine methyl ester in the form of a colorless oil.

1.8 g of N-(p-cyanobenzoyl)-3-[p-(tert-butoxycarbonylmethoxy)phenyl]-D-alanine methyl ester was obtained as a colorless resin from 1.65 g of 3-[p-(tert-butoxycarbonylmethoxy)phenyl]-D-alanine methyl ester after reaction with 0.97 g of 4-cyanobenzoyl chloride and 1.08 g of triethylamine in chloroform and after the usual working up and chromatography on silica gel with ether/petroleum ether 1:1.

EXAMPLE 71

462 mg of N-(p-amidinobenzoyl)-3-[p-(tert-butoxycarbonylmethoxy)phenyl]-D-alanine methyl ester were left to stand in a mixture of 4.5 ml of methylene chloride and 3.5 ml of trifluoroacetic acid at room temperature for 2 hours. The mixture was then concentrated in vacuo, and the residue was stirred with diethyl ether. The resulting orange powder was chromatographed on silica gel with water and subsequently with water/acetonitrile 9:1. The 160 mg of yellow crystals of p-[(R)-2-(p-amidinobenzamido)-2-methoxycarbonylethyl]phenoxyacetic acid trifluoroacetate obtained after removal of the solvent melted at 153°–155° C. Optical rotation was $[\alpha]_D^{20} = +48.6°$ (methanol, c=0.97).

EXAMPLE 72

In analogy to Example 2, 98 mg of N-(p-amidinobenzoyl)-3-(p-carbozymethozyphenyl)-D-alanine monohydrate were obtained in the form of colorless crystals of melting point 191°–193° C. from 232 mg of the trifluoroacetate salt of p-[(R)-2-(p-amidinobenzamido)-2-methozycarbonylethyl]phenozyacetic acid by hydrolysis with methanolic aqueous sodium hydroxide solution and subsequent neutralization with p-toluenesulphonic acid.

EXAMPLE 73

In analogy to Example 1, the acetate salt of methyl (E)-p-[2-(p-amidinobenzamido)ethyl]-β-methylcinnamate was obtained from methyl p-[2-(p-cyanobenzamido)ethyl]-β-methylcinnamate. Melting point 196° C.

The starting material was prepared from methyl p-(2-aminoethyl)-β-methylcinnamate hydrochloride (EP-Al 25,331) and p-cyanobenzoyl chloride. Melting point 162°–164° C.

EXAMPLE 74

190 mg of methyl (E)-p-[2-(p-amidinobenzamido)ethyl]-β-methylcinnamate were obtained after hydrogenation in methanol in the presence of 10% Pd/C under atmospheric pressure at room temperature after 24 hours 113 mg of crystalline acetate of methyl rac-p-[2-(p-amidinobenzamido)ethyl]-β-methyl-hydrocinnamate.

EXAMPLE 75

113 mg of methyl rac-p-[2-(p-amidinobenzamido)ethyl]-β-methylhydrocinnamate were dissolved in methanol/2 N sodium hydroxide solution and stored at room temperature overnight. The residue after removal of the solvent was dissolved in hot methanol, and ether was added. The crystals precipitated were filtered off with suction and dried over high vacuum, resulting in 52 mg of the sodium salt of rac-p-[2-(p-amidinobenzamido)ethyl]-β-methylhydrocinnamic acid. The melting point in dimethyl formamide was greater than 200° C.

EXAMPLE 76

0.4 ml of triethylamine, followed by a solution of 300 mg of 4-nitrophenyl 4-guanidinobenzoate hydrochloride in dimethylformamide, were added to a solution of 219 mg of methyl 4-(2-aminoethyl)phenoxyacetate hydrochloride in dimethylformamide (10 ml). After 5 hours at room temperature, the solvent was removed, and the residue was chromatographed on 20 g of silica gel with ethyl acetate/acetone/water/acetic acid 9:5:1:1. 103 mg of the acetate salt of methyl p-[2-(p-guanidinobenzamido)ethyl]phenoxyacetate were obtained in the form of a pale yellow resin.

EXAMPLE 77

In analogy to Example 1, the acetate salt of methyl α-[2-(p-amidinophenyl)acetamido]-p-tolyloxyacetate was obtained from methyl α-[2-(p-cyanophenyl)acetamido]-p-tolyloxyacetate. Melting point 97° C. (from methanol).

The starting material was prepared as follows (compare German Offenlegungsschrift 2,320,387):

1.61 g of methyl p-aminomethylphenoxyacetate hydrochloride were reacted with 2.32 g of p-cyanophenylacetic acid in the presence of 1.79 g of 2-chloro-4,6-dimethoxy-1,3,5-triazine as described in Example 1. Working up and recrystallization of the crude product from dichloro- methane/ether resulted in 680 mg of methyl α-[2-(p- cyanophenyl)acetamido]-p-tolyloxyacetate with melting point 147° C.

EXAMPLE 78

200 mg of methyl α-[2-(p-amidinophenyl)acetamido]-p-tolyloxyacetate acetate were stored in 4 ml methanol/2 N sodium hydroxide solution 3:1 at room temperature overnight. The crystals which precipitated were washed with water/ether and dried under high vacuum. 117 mg of the sodium salt of p-[2-(p-amidinophenyl)acetamido]-p-tolyloxyacetic acid were thus obtained. Melting point >200° C.

EXAMPLE 79

In analogy to Example 1, N-benzyl-N-[p-[2-(p-amidinobenzamido)ethyl]phenyl]glycine methyl ester, melting point 193°-194° C. (from ethanol), was obtained from N-benzyl-N-[p-[2-(p-cyanobenzamido)ethyl]phenyl]glycine methyl ester.

Preparation of the starting material was as follows (see German Offenlegungsschrift 3,622,865, incorporated herein by reference):

920 mg of N-[p-(2-aminoethyl)phenyl]glycine methyl ester sulphate were reacted in analogy to Example 3 with 4-cyanobenzoyl chloride to give N-[p-[2-(p-cyanobenzamido) ethyl]phenyl]glycine methyl ester, melting point 161°-162° C. (from toluene).

1.2 ml of triethylamine and 3 ml of benzyl chloroformate (50% in toluene) were added to a solution of 675 mg of N-[p-[2-(p-cyanobenzamido)ethyl]phenyl]glycine methyl ester in 15 ml of chloroform. The reaction mixture was maintained at 50° C. overnight. After working up and chromatography on silica gel with ether/petroleum ether 2:1, 500 mg of crystalline N-benzyl-N-[p-[2-(p-cyanobenzamido)ethyl]phenyl]glycine methyl ester, melting point 123°-124° C., were isolated.

EXAMPLE 80

106 mg of p-[2-(p-guanidinobenzamido)ethyl]phenoxyacetic acid were obtained from 200 mg of methyl p-[2-(p-guanidinobenzamido)ethyl]phenoxyacetate acetate (Example 76) by basic hydrolysis as described in Example 1. The melting point was greater than 200° C. ($H_2O$).

EXAMPLE 81 a) 3.14 g of t-butyl p-[(R)-2-(p-cyanobenzamido)-3-hydroxypropyl]phenoxyacetate were successively reacted with $H_2S$/pyridine, $CH_3I$/acetone and $NH_4OAc$/methanol as described in Example 1. After chromatography on silica gel with water/methanol (100:0 1:1), 1.2 g of t-butyl p-[(R)-2-(p-amidinobenzamido)-3-hydroxypropyl]phenoxyacetate were obtained in the form of a white foam. MS: 428 (M+1).

b) 427 mg of the product from Example 81a were hydrolyzed with 2 N HCl/THF (1:1) at 50° C. and subsequently chromatographed on silica gel with water/methanol (100:0 0:100) to yield 136 mg of p-[(R)-2-(p-amidinobenzamido)-3-hydroxypropyl]phenoxyacetic acid having a melting point 238°-240° C.

Preparation of the starting material

Reduction of 7.63 g of 3-[p-(tert-butoxycarbonylmethoxy) phenyl]-N-(p-cyanobenzoyl)-D-alanine methyl ester (Example 70) with lithium borohydride in methanol resulted, after working up and chromatography on silica gel with $CH_2Cl_2$/MeOH (100:0 9:1), in 3.14 g of t-butyl p-[(R)-2-(p-cyanobenzamido)-3-hydroxypropyl]phenoxyacetate in the form of a white foam, IR =3389, 2231, 1752, 1645 $cm^{-1}$.

EXAMPLE 82

205 mg of dimethyl [4-(p-amidino-N-methylbenzamido) acetyl-o-phenylenedioxy]diacetate of melting point 177°-178° C. were isolated after reaction of 1.4 g of dimethyl [4-(p-cyano-N-methylbenzamido)acetyl-o-phenylenedioxy]diacetate as described in Example 1 and after chromatography on silica gel with water/methanol (100:0→4:1).

Preparation of the starting material 1) 1.65 g of 4-cyanobenzoyl chloride were added to a solution of 2.17 g of adrenalone hydrochloride in 26 ml of DMF/pyridine (10:3). After 1 hour the reaction mixture was poured onto ice-water; the mixture was acidified with 2 N hydrochloric acid and stirred for 35 minutes, and the crystals which had precipitated were filtered off. Chromatography on silica gel with $CH_2Cl_2/CH_3OH$ (100:0 98:2) resulted in 1.06 g of α-(p-cyano-N-methylbenzamido)-3,4-dihydroxy-acetophenone of melting point 223°-225° C. (decomposition).

2) A solution of 3.9 g of α-(p-cyano-N-methylbenzamido)-3,4-dihydroxy-acetophenone in 50 ml of acetone was heated in the presence of 3.47 g of potassium carbonate at 65° C. for 1 hour. Then, at room temperature, 4.8 g of methyl bromoacetate were added dropwise. The reaction mixture was maintained at room temperature for 12 hours and at 50° C. for 6 hours. The solvents were subsequently removed, the residue was stirred with ice-water, and the precipitate which had separated out was filtered off. The gummy solid was recrystallized from ether/ethyl acetate (2:1), resulting in 4.4 g of colorless dimethyl [4-(p-cyano-N-methylbenzamido)acetyl-o-phenylene-dioxy]diacetate of melting point 115°-117° C.

EXAMPLE 83

A solution of 600 mg of dimethyl [4-(p-amidino-N-methyl benzamido)acetyl-o-phenylenedioxy]diacetate (Example 82) in 20 ml of 10% aqueous acetic acid was maintained at the boiling point overnight. It was subsequently concentrated, and the residue was induced to crystallize with ethanol. Recrystallization from water/ethanol resulted in 110 mg of [4-(p-amidino-N-methylbenzamido)acetyl-o-phenylenedioxy]diacetic acid of melting point 230° C. (sintering at 190° C.).

EXAMPLE 84

The following were obtained as in Example 1 from 5.40 g of methyl p-[N-(p-cyanobenzoyl)-(RS)-alanyl]-phenoxyacetate a) 1.75 g of methyl p-[N-(p-amidinobenzoyl)-(RS)alanyl]phenoxyacetate hydrochloride, IR bands (KBr) at 3377, 3049, 1755, 1681, 1600, 1540, 1509, 1483, 1215, 971 $cm^{-1}$ and b) 700 mg of methyl p-[(all-RS)-2-(p-amidinobenzamido)-1-methyldithio-propyl]phenoxyacetate hydrochloride, IR bands (KBr) at 3249, 3036, 1744, 1680, 1639, 1542, 1484, 1210, 1177, 1079, 708 $cm^{-1}$.

The starting material was obtained by reaction of methyl p-(p-cyanobenzamidoacetyl)phenoxyacetate (melting point 200°-203°; see Example 25) with butyllithium/methyl iodide in 1,2-dimethoxyethane at room temperature. Melting point 190°-192°.

EXAMPLE 85

500 mg of methyl p-(p-amidinobenzoylalanyl)-phenoxyacetate hydrochloride (Example 84) were stirred in 10 ml of 2 N hydrochloric acid at 0°–5° for 1 hour. The crystals which had precipitated were filtered off with suction and dried in vacuo. 250 mg of pure crystalline p-[N-(p-amidinobenzoyl)-(R,S)-alanyl]-phenoxyacetic acid hydrochloride, melting point 146°–151° were obtained.

EXAMPLE 86

390 mg of amorphous methyl p-[2-[p-amidino-N-(p-carbomethoxybenzyl)benzamido]-1-hydroxyethyl]-phenoxyacetate hydrochloride were obtained as in Example 11 from 502 mg of methyl p-[2-[p-cyano-N-(p-carbomethoxybenzyl)benzamido]-1-hydroxyethyl]-phenoxyacetate. IR bands (KBr) at 2922, 2853, 1744, 1718, 1680, 1608, 1511, 1461, 1281, 1110, 1016, 857 cm$^{-1}$.

The starting material was obtained by reaction of methyl p-[2-[N-(p-carbomethoxybenzyl)amino]-1-hydroxyethyl]phenoxyacetate (melting point 97°–100°, obtained by reaction of methyl 4-formylbenzoate with methyl 4-(2-amino-1-hydroxyethyl)phenoxyacetate and sodium cyanoborohydride) with p-cyanobenzoyl chloride in pyridine. Amorphous, IR bands (KBr) at 3429, 2953, 2230, 1759, 1720, 1612, 1510, 1436, 1285, 1110, 1017, 850, 758 cm$^{-1}$.

EXAMPLE 87

110 mg of colorless amorphous p-[2-[p-amidino-N-(p-carboxybenzyl)benzamido]-1-hydroxyethyl]phenoxyacetic acid were obtained as in Example 12 from 190 mg of methyl p-[2-[p-amidino-N-(p-carbomethoxybenzyl)benzamido]-1-hydroxyethyl]phenoxyacetate hydrochloride (Example 86). IR bands (KBr) at 3387, 2933, 1685, 1610, 1510, 1412, 1222, 1177, 1064, 1016 cm$^{-1}$.

EXAMPLE 88

540 mg of pure amorphous methyl p-[p-amidino-N-(p-carbomethoxybenzyl)benzamidoacetyl]phenoxyacetate hydrochloride were obtained as in Example 11 from 800 mg of methyl P-[p-cyano-N-(p-carbomethoxybenzyl)benzamidoacetyl]phenoxyacetate hydrochloride. IR Bands (KBr) at 3377, 2952, 1757, 1722, 1681, 1636, 1599, 1536, 1438, 1285, 1171, 835 cm$^{-1}$.

The starting material was obtained by reaction of methyl p-[2-[p-cyano-N-(p-carbomethoxybenzyl)benzamido]-1-hydroxyethyl]phenoxyacetate (see Example 86) with manganese dioxide in chloroform. Amorphous, IR Bands (KBr) at 2954, 2230, 1760, 1720, 1689, 1642, 1601, 1509, 1436, 1356, 1110, 844, 757 cm$^{-1}$.

EXAMPLE 89

238 mg of pure amorphous p-[p-amidino-N-(p-carboxybenzyl)benzamidoacetyl]phenoxyacetic acid were obtained as in Example 12 from 310 mg of methyl p-[p-amidino-N-(p-carbomethoxybenzyl)benzamidoacetyl]-phenoxyacetate hydrochloride (Example 88). IR Bands (KBr) at 2924, 2853, 1685, 1606, 1464, 1378, 1230, 1174 cm$^{-1}$.

EXAMPLE 90

330 mg of amorphous p-[(RS)-2-(p-amidinobenzamido)-1-methoxyethyl]phenoxyacetic acid hydrochloride were obtained as in Example 11 from 500 mg of methyl p-[(RS)-2-(p-cyanobenzamido)-1-methoxyethyl]phenoxyacetate. IR Bands (KBr) at 3252, 3052, 1756, 1681, 1643, 1545, 1485, 1211, 1078, 714 cm$^{-1}$.

The starting material was obtained by reaction of methyl p-[2-(p-cyanobenzamido)-1-hydroxyethyl]-phenoxyacetate (Example 21) with butyllithium/methyl iodide in 1,2-dimethoxyethane, IR Bands (KBr) at 3350, 2933, 2230, 1759, 1655, 1610, 1511, 1176, 1081, 834 cm$^{-1}$.

EXAMPLE 91

33 mg of p-[(RS)-2-(p-amidinobenzamido)-1-methoxyethyl]phenoxyacetic acid were obtained as in Example 12 from 63 mg of methyl p-[(RS)-2-(p-amidinobenzamido)-1-methoxyethyl]phenoxyacetate hydrochloride (Example 90), IR Bands (KBr) at 3270, 2932, 1674, 1609, 1511, 1482, 1424, 1336, 1235, 1105, 721 cm$^{-1}$.

EXAMPLE 92

90 mg of p-[(all-RS)-2-(p-amidinobenzamido)-1-methyldithiopropyl]phenoxyacetic acid hydrochloride were obtained as in Example 85 from 100 mg of methyl p-[(all-RS)-2-(p-amidinobenzamido)-1-methyldithiopropyl]phenoxy acetate hydrochloride (Example 84b), IR Bands (KBr) at 3042, 2926, 1679, 1638, 1541, 1508, 1482, 1210, 1177, 1072, 858 cm$^{-1}$.

EXAMPLE 93

In analogy to Example 11, methyl p-[(RS)-2-(p-amidinobenzamido)-1-(2-dimethylaminoethoxy)ethyl]-phenoxyacetate hydrochloride was obtained from methyl p-[(RS)-2-(p-cyano benzamido)-1-(2-dimethylaminoethoxy)ethyl]phenoxyacetate.

The starting material was prepared by reaction of methyl p-[2-(p-cyanobenzamido)-1-hydroxyethyl]-phenoxyacetate (Example 21) with butyllithium/methyl iodide in 1,2-dimethoxyethane.

EXAMPLE 94

The following compounds were prepared in a manner analogous to the preceding examples:
a) p-[(S)-2-(p-amidinobenzamido)propyl]phenoxyacetic acid,
b) p-[p-amidino-N-[(RS)-p-carboxymethoxy-β-hydroxyphenethyl]benzamido]-p-toluylic acid,
c) methyl rac-p-[2-(p-amidinobenzamido)-1-oxopropyl]phenoxyacetate,
d) rac-p-[2-(p-amidinobenzamido)-1-oxopropyl]-phenoxyacetic acid,
e) p-(p-amidino-N-methylbenzamidoacetyl)phenoxyacetic acid,
f) methyl p-[(E)-2-(p-amidinophenylcarbamoyl)-vinyl]phenoxyacetate.

EXAMPLE 95

In analogy to Example 11, 38 mg of methyl p-[(E)-2-(p-amidinobenzamido)vinyl]phenoxyacetate hydrochloride were obtained from 114 mg of methyl p-[2-(p-cyanophenyl)2-oxazolidin-5-yl)phenoxyacetate. IR Bands (KBr) at 3424, 1747, 1609, 1508, 1484, 1437, 1216, 1177, 1080 cm$^{-1}$.

The starting material was obtained by treating methyl p-[(RS)-1-hydroxy-2-(p-cyanobenzamido)ethyl]-phenoxyacetate (Example 21) with acidic alumina in xylene at the boiling point.

EXAMPLE 96

In analogy to Example 11, 880 mg of methyl p-[(RS)-1-acetoxy-2-(p-amidinobenzamido)ethyl]phenoxyacetate hydrochloride were obtained from 1.59 g of methyl p-[(RS)-1-acetoxy-2-(p-cyanobenzamido)ethyl]phenoxyacetate. IR Bands (KBr) at 3374, 3084, 1739, 1680, 1646, 1545, 1512, 1485, 1233, 1078, 711 cm$^{-1}$.

The starting material was obtained by reaction of methyl P-[(RS)-1-hydroxy-2-(p-cyanobenzamido)ethyl]phenoxyacetate (Example 21) with acetic anhydride/pyridine. IR Bands (KBr) at 3360, 2954, 2230, 1740, 1661, 1612, 1540, 1513, 1373, 1081, 1032, 833 cm$^{-1}$.

EXAMPLE 97

In analogy to Example 11, 860 mg .of methyl p-[2-(p-amidino benzoylmethylamino)ethyl]phenoxyacetate hydrochloride were obtained from 1.30 g of methyl p-[2-(p-cyanobenzoylmethylamino)ethyl]phenoxyacetate. IR Bands (KBr) at 3031, 1756, 1680, 1612, 1511, 1408, 1208, 1077, 858 cm$^{-1}$.

The starting material was obtained by reaction of p-[2-(p-cyanobenzoylmethylamino)ethyl]phenol with methyl bromoacetate in acetone in the presence of potassium carbonate. The melting point was 113°–115° C.

p-[2-(p-Cyanobenzoylmethylamino)ethyl]phenol was obtained by reaction of N-methyltyramine with p-cyanobenzoyl chloride in pyridine. The melting point was 151°–152° C.

EXAMPLE 98

In analogy to Example 12, 580 mg of p-[2-(p-amidinobenzoyl methylamino)ethyl]phenoxyacetic acid hydrochloride were obtained from 640 mg of methyl p-[2-(p-amidinobenzoylmethylamino)ethyl]phenoxyacetate hydrochloride. IR Bands (KBr) at 3382, 3042, 1680, 1609, 1511, 1405, 1210, 1074 cm$^{-1}$.

EXAMPLE 99

In analogy to Example 11, 166 mg of methyl p-(6-amidino nicotinamidoacetyl)phenoxyacetate hydrochloride were obtained from 480 mg of methyl p-(6-cyanonicotinamidoacetyl)phenoxyacetate.

The starting material was obtained by reaction of methyl P-[(RS)-2-(6-cyanonicotinamido)-1-hydroxyethyl]phenoxyacetate with manganese dioxide in chloroform, which in turn was produced by reaction of methyl 4-(2-amino-1-hydroxyethyl) phenoxyacetate hydrochloride (melting point 123°–125° C.) with 6-cyanonicotinic acid and ethyl chloroformate/4ethylmorpholine (melting point 131°–132° C.).

EXAMPLE 100

In analogy to Example 85, 115 mg of p-(6-amidinonicotin amidoacetyl)phenoxyacetic acid hydrochloride were obtained from 125 mg of methyl p-(6-amidinonicotinamidoacetyl)phenoxyacetate hydrochloride. IR Bands (KBr) at 3337, 3249, 3069, 1692, 1637, 1599, 1535, 1422, 1178, 1059, 832 cm$^{-1}$.

EXAMPLE 101

The following were prepared in analogy to Example 100:
a) methyl P-(5-amidinonicolinamidoacetyl)phenoxyacetate hydrochloride, IR Bands (KBr) at 3380, 3265, 2954, 1760, 1657, 1598, 1519, 1221, 1074, 987 cm$^{-1}$
b) p-(5-amidinonicolinamidoacetyl)phenoxyacetic acid hydrochloride, IR Bands (KBr) at 3598, 3351, 3073, 2908, 1683, 1660, 1598, 1524, 1360, 1178, 1072, 992 cm$^{-1}$.

EXAMPLE 102

In analogy to Example 11, 200 mg of methyl α-(p-amidinobenzamidoxy)-p-tolyloxyacetate hydrochloride were obtained from 550 mg of methyl α-(p-cyanobenzamidoxy)-p-tolyloxyacetate. IR Bands (KBr) at 3128, 1738, 1668, 1511, 1477, 1431, 1231, 1077, 714 cm$^{-1}$.

The starting material was obtained by reaction of methyl 4-aminoxymethyl-phenoxyacetate with p-cyanobenzoyl chloride in pyridine. Melting point 173°–175° C.

EXAMPLE 103

A compound of the formula I may be used as one of the active ingredients in a tablet formulated using standard techniques. For example, tablets may be formulated as follows:

| A | Per tablet |
| --- | --- |
| Active compound | 200 mg |
| Microcrystalline cellulose | 155 mg |
| Maize starch | 25 mg |
| Talc | 25 mg |
| Hydroxypropylmethylcellulose | 20 mg |
| | 425 mg |
| Example B | |
| B | Per capsule |
| Active compound | 100.0 mg |
| Maize starch | 20.0 mg |
| Lactose | 95.0 mg |
| Talc | 4.5 mg |
| Magnesium stearate | 0.5 mg |
| | 220.0 mg |

Many modifications and variations of this invention may be made without departing from its scope, as is apparent to those skilled in the art. The specific embodiments described herein are offered by way of example only, and the invention is to be limited only by the terms of the appended claims.

It is claimed:

1. A compound of the formula $$R^1-A-(W)_a-X-(CH_2)_b-(Y)_c-B-Z-COOR \quad (I)$$

in which
A is

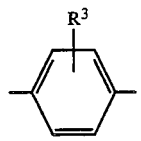

B is

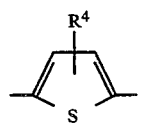

W is —CH$_2$—, —CH$_2$CH$_2$—, —CH=CH—, —CH=CH—CH$_2$—, —(CH$_2$)$_3$—, —CH$_2$CH(CH$_3$)—, —COCH$_2$—, —CH(OH)CH$_2$— or —CH$_2$COCH$_2$—;

X is —CONR$^2$—, —NR$^2$CO—, —SO$_2$NR$^2$— or —NR$^2$SO$_2$—;

Y is —CH$_2$CH$_2$—, —CH$_2$CH$_2$O—, —OCH$_2$—, —CH(CH$_3$)CH$_2$—, —CH=CH—, —CH$_2$—CH=CH—, —C(Q$^1$, Q$^2$)—CO(CH$_2$)$_4$—, —CH$_2$—, —CH$_2$CH$_2$CH$_2$—, —CH(CH$_3$)CH$_2$CH$_2$—, —CH$_2$COCH$_2$—, —C(Q$^1$,Q$^2$)—CH(OH)—, —C(Q$^1$,Q$^2$)—CH(SSCH$_3$)—, —CH(CH$_2$OH)CH$_2$ or —CH(COOR)CH$_2$—, wherein the carbonyl groups may be in the form of oxime, oxime ether, ketal or thioketal or enol ether and the hydroxyl groups may be in the form of lower alkyl ether, di(lower alkyl)amino-lower-alkyl ether or of ester of lower alkanecarboxylic acids;

Z is —OCH$_2$—, —NR$^6$CH$_2$—, —CH$_2$CH$_2$—, —CH(CH$_3$)CH$_2$—, —CH$_2$—, —CH=CH— or —C(CH$_3$)=CH—;

R is hydrogen, lower alkyl, phenyl or phenyl-lower alkyl;

Q$^1$ and Q$^2$ are hydrogen or lower alkyl or form, together with the C atom to which they are bonded, a 3- to 6-membered saturated ring;

R$^1$ is amidino or guanidino;

R$^2$ is hydrogen, lower alkyl, phenyl-lower-alkyl, phenyl-lower-alkyl which is substituted in the phenyl moiety by amino, amidino or —COOR, or a radical —CH$_2$COOR or —Y—B—X—COOR;

R$^3$ is hydrogen, lower alkyl, lower alkoxy, halogen, lower carbalkoxy, amino, lower alkylamino, di-lower-alkylamino or amidino;

R$^4$ is hydrogen, lower alkyl, lower alkoxy, halogen, lower carbalkoxy, amino, lower alkylamino, di-lower-alkyl-amino or a radical —Z—COOR or —CH=CH(CH$_2$)$_n$COOR;

R$^6$ is hydrogen, lower alkyl or benzyl;

n is an integer of 0–4;

a, c and d each are 0 or 1;

b is an integer of 0–2, where a and b are 0 when c is 1, and c is 0 when a or b is different from 0;

or the physiologically acceptable salts thereof.

2. The compound according to claim 1 having the formula

R$^{1l}$—A—X—Y—B—Z—COOR (Ia), wherein R$^1$, A, X, Y, B, Z, and R are as defined in claim 1.

3. The compound according to claim 1 having the formula

R$^1$—A—W—X—(CH)$_b$—B—Z—COOR (Ib)

wherein R$^1$, A, W, X, b, B, Z, and R are as defined in claim 1.

4. The compound of claim 2 wherein Y is —CH$_2$CH$_2$—, —CH$_2$CH$_2$O—, —CH(CH$_3$)CH$_2$—, —CH=CH—, —CH$_2$—CH=CH—, —CH$_2$CO—, —CH$_2$—, —CH$_2$CH$_2$CH$_2$—, —CH(CH$_3$)CH$_2$CH$_2$—, —CH$_2$COCH$_2$—, —CH$_2$CHOH—, —CH(CH$_2$OH)CH$_2$— or —CH(COOR)CH$_2$—, wherein the carbonyl groups may be in the form of oxime, ketal or thioketal or enol ether and the hydroxyl groups may be in the form of lower alkyl ether or of ester of lower alkanecarboxylic acids.

5. The compound of claim 4 wherein R$^1$ is amidino.

6. The compound of claim 5 wherein X is —CONR$^2$—.

7. The compound of claim 6 wherein Z is —CH(CH$_2$)CH$_2$— or —CH(CH$_3$)=CH—.

8. The compound of claim 7 wherein Z is —CH(CH$_3$)=CH—.

9. The compound of claim 8 wherein Y is —CH(CH$_2$)CH$_2$—.

10. The compound of claim 9 wherein R is hydrogen or lower alkyl.

11. The compound of claim 10, ethyl (E)-5-[(RS)-2-(p-amidinobenzamido)propyl]-β-methyl-2-thiopheneacrylate.

12. The compound of claim 10, (E)-5-[(RS)-2-(p-amidinobenzamido)propyl]-β-methyl-2-thiopheneacrylic acid.

13. The compound of claim 7 wherein Z is —CH(CH$_3$)CH$_2$—.

14. The compound of claim 13 wherein Y is —CH(CH$_3$)CH$_2$—.

15. The compound of claim 14 wherein R is hydrogen or lower alkyl.

16. The compound of claim 14 ethyl (RS)-5-[(RS)-2-(p-amidinobenzamido)propyl]-β-methyl-2-thiophenepropionate.

17. The compound of claim 14, (RS)-5-[(RS)-2-(p-amidinobenzamido)propyl]-β-methyl-2-thiophenepropionic acid.

18. A pharmaceutical composition comprising a compound of the formula

R$^1$—A—(W)$_a$—X—(CH$_2$)$_b$(Y)$_c$—B—Z—COOR (I)

in which

A is

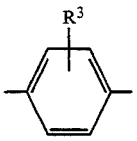

B is

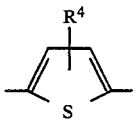

W is —CH$_2$—, —CH$_2$CH$_2$—, —CH=CH—, —CH=CH—CH$_2$—, —(CH$_2$)$_3$—, —CH$_2$CH(CH$_3$)—, —COCH$_2$—, —CH(OH)CH$_2$— or —CH$_2$COCH$_2$—;

X is —CONR$^2$—, —NR$^2$CO—, —SO$_2$NR$^2$— or —NR$^2$SO$_2$—;

Y is —CH$_2$CH$_2$—, —CH$_2$CH$_2$O—, —OCH$_2$—, —CH(CH$_3$)CH$_2$—, —CH=CH—, —CH$_2$—CH=CH—, —C(Q$^1$, Q$^2$)—CO(CH$_2$)$_d$—, —CH$_2$—, —CH$_2$CH$_2$CH$_2$—, —CH(CH$_3$)CH$_2$CH$_2$—, —CH$_2$COCH$_2$—, —C(Q$^1$,Q$^2$)—CH(OH)—, —C(Q$^1$,Q$^2$)—CH(SSCH$_3$)—, —CH(CH$_2$OH)CH$_2$— or —CH(COOR)CH$_2$—, wherein the carbonyl groups may be in the form of oxime, oxime ether, ketal or thioketal or enol ether and the hydroxyl groups may be in the form of lower alkyl ether, di(lower alkyl)amino-lower-alkyl ether or of ester of lower alkanecarboxylic acids;

Z is —OCH₂—, —NR⁶CH₂—, —CH₂CH₂—, —CH(CH₃)CH₂—, —CH₂—, —CH=CH— or —C(CH₂)=CH—;

R is hydrogen, lower alkyl, phenyl or phenyl-lower alkyl;

Q¹ and Q² are hydrogen or lower alkyl or form, together with the C atom to which they are bonded, a 3- to 6-membered saturated ring;

R¹ is amidino or guanidino;

R² is hydrogen, lower alkyl, phenyl-lower-alkyl, phenyl-lower-alkyl which is substituted in the phenyl moiety by amino, amidino or —COOR, or a radical —CH₂COOR or —Y—B—X—COOR;

R³ is hydrogen, lower alkyl, lower alkoxy, halogen, lower carbalkoxy, amino, lower alkylamino, di-lower-alkylamino or amidino;

R⁴ is hydrogen, lower alkyl, lower alkoxy, halogen, lower carbalkoxy, amino, lower alkylamino, di-lower-alkyl-amino or a radical —Z—COOR or —CH=CH(CH₂)ₙCOOR;

R⁶ is hydrogen, lower alkyl or benzyl;

n is an integer of 0–4;

a, c and d each are 0 or 1;

b is an integer of 0–2, where a and b are 0 when c is 1, and c is 0 when a or b is different from 0; or the physiologically acceptable salts thereof; together with one or more excipients or carriers.

19. A method of treating thromboses, apoplexy, myocardial infarct, inflammations and arteriosclerosis comprising administering an effective amount of a compound of the formula $$R^1-A-(W)_a-X-(CH_2)_b-(Y)_c-B-Z-COOR \quad (I)$$

in which

A is

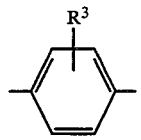

B is

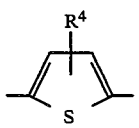

W is —CH₂—, —CH₂CH₂—, —CH=CH—, —CH=CH—CH₂—, —(CH₂)₃—, —CH₂CH(CH₃)—, —COCH₂—, —CH(OH)CH₂— or —CH₂COCH₂—;

W is —CONR²—, —NR²CO—, —SO₂NR²— or —NR²SO₂—;

Y is —CH₂CH₂—, —CH₂CH₂O—, —OCH₂—, —CH(CH₃)CH₂—, —CH=CH—, —CH₂—CH=CH—, C(Q¹, Q²)—CO(CH₂)_d—, —CH₂—, —CH₂CH₂CH₂—, —CH(CH₃)CH₂CH₂—, —CH₂COCH₂—, —C(Q¹,Q²)—CH(OH)—, —C(Q¹, Q²)— CH(SSCH₃)—, —CH(CH₂OH)CH₂— or —CH(COOR)CH₂—, wherein the carbonyl groups may be in the form of oxime, oxime ether, ketal or thioketal or enol ether and the hydroxyl groups may be in the form of lower alkyl ether, di(lower-alkyl)amino-lower-alkyl ether or of ester of lower alkanecarboxylic acids; is —OCH₂—, —NR⁶CH₂—, —CH₂CH₂—, —CH(CH₃)CH₂—, —CH₂—, —CH=CH— or —C(CH₃)=CH—;

R is hydrogen, lower alkyl, phenyl or phenyl-lower alkyl;

Q¹ and Q² are hydrogen or lower alkyl or form, together with the C atom to which they are bonded, a 3- to 6-membered saturated ring;

R¹ is amidino or guanidino;

R² is hydrogen, lower alkyl, phenyl-lower-alkyl, phenyl-lower-alkyl which is substituted in the phenyl moiety by amino, amidino or —COOR, or a radical —CH₂COOR or —Y—B—X—COOR;

R³ is hydrogen, lower alkyl, lower alkoxy, halogen, lower carbalkoxy, amino, lower alkylamino, di-lower-alkylamino or amidino;

R⁴ is hydrogen, lower alkyl, lower alkoxy, halogen, lower carbalkoxy, amino, lower alkylamino, di-lower-alkyl-amino or a radical -Z-COOR or —CH=CH(CH₂)ₙCOOR;

R⁶ is hydrogen, lower alkyl or benzyl;

n is an integer of 0–4;

a, c and d each are 0 or 1;

b is an integer of 0–2, where a and b are 0 when c is 1, and c is 0 when a or b is different from 0;

or the physiologically acceptable salts thereof.

* * * * *

UNITED STATES PATENT AND TRADEMARK OFFICE
CERTIFICATE OF CORRECTION

PATENT NO. : 5,399,585
DATED : March 21, 1995
INVENTOR(S) : Leo Alig, et al.

It is certified that error appears in the above-indentified patent and that said Letters Patent is hereby corrected as shown below:

In claim 1, column 28, line 45, delete "$R^1-A-(W)_a-X-(CH_2)_b-(Y)_c-B-Z-COOR$ (I)" and insert -- $R^1-A-(W)_a-X-(CH_2)_b-(Y)_c-B-Z-COOR$ (I) --.

In claim 1, column 29, line 5, delete "$-C(Q^1,Q^2)-CO(CH_2)_4-$" and insert -- $-C(Q^1,Q^2)-CO(CH_2)_d-$ --.

In claim 2, column 29, line 45, delete "$R^{11}-A-X-Y-B-Z-COOR$ (Ia)," and insert -- $R^1-A-X-Y-B-Z-COOR$ (Ia), --.

In claim 3, column 29, line 53, delete "$R^1-A-W-X-(CH)_b-B-Z-COOR$ (Ib)" and insert -- $R^1-A-W-X-(CH_2)_b-B-Z-COOR$ (Ib) --.

In claim 7, column 30, line 2, delete "$CH(CH_2)CH_2-$" and insert -- $-CH(CH_3)CH_2-$ --.

In claim 9, column 30, line 6, delete "$-CH(CH_2)CH_2-$" and insert -- $-CH(CH_3)CH_2-$ --.

UNITED STATES PATENT AND TRADEMARK OFFICE
CERTIFICATE OF CORRECTION

PATENT NO. : 5,399,585
DATED : March 21, 1995
INVENTOR(S) : Leo Alig, et al.

It is certified that error appears in the above-indentified patent and that said Letters Patent is hereby corrected as shown below:

In claim 18, column 30, line 31, delete "$R^1\text{-}A\text{-}(W)_a\text{-}X\text{-}(CH_2)_b(Y)_c\text{-}B\text{-}Z\text{-}COOR$    (I)" and insert -- $R^1\text{-}A\text{-}(W)_a\text{-}X\text{-}(CH_2)_b\text{-}(Y)_c\text{-}B\text{-}Z\text{-}COOR$    (I) --.

In claim 18, column 31, line 3, delete "$\text{-}C(CH_2)\text{=}CH\text{-}$" and insert -- $\text{-}C(CH_3)\text{=}CH\text{-}$ --.

In claim 19, column 32, line 12, delete "W" and insert -- X --.

Signed and Sealed this

Eighteenth Day of July, 1995

Attest:

BRUCE LEHMAN

Attesting Officer

Commissioner of Patents and Trademarks